US011850055B2

(12) United States Patent
Hiratsuka et al.

(10) Patent No.: US 11,850,055 B2
(45) Date of Patent: Dec. 26, 2023

(54) ELECTROENCEPHALOGRAPHIC DATA ANALYSIS SYSTEM, INFORMATION PROCESSING TERMINAL, ELECTRONIC DEVICE, AND METHOD OF PRESENTING INFORMATION FOR DEMENTIA EXAMINATION

(71) Applicant: MAXELL, LTD., Kyoto (JP)

(72) Inventors: Yukie Hiratsuka, Tokyo (JP); Chiyo Ohno, Tokyo (JP)

(73) Assignee: MAXELL, LTD., Kyoto (JP)

( * ) Notice: Subject to any disclaimer, the term of this patent is extended or adjusted under 35 U.S.C. 154(b) by 1027 days.

(21) Appl. No.: 16/608,703

(22) PCT Filed: Apr. 28, 2017

(86) PCT No.: PCT/JP2017/016991
§ 371 (c)(1),
(2) Date: Oct. 25, 2019

(87) PCT Pub. No.: WO2018/198332
PCT Pub. Date: Nov. 1, 2018

(65) Prior Publication Data
US 2021/0113139 A1 Apr. 22, 2021

(51) Int. Cl.
*A61B 5/378* (2021.01)
*A61B 5/38* (2021.01)
(Continued)

(52) U.S. Cl.
CPC ............ *A61B 5/378* (2021.01); *A61B 5/0006* (2013.01); *A61B 5/291* (2021.01); *A61B 5/372* (2021.01);
(Continued)

(58) Field of Classification Search
CPC ......... A61B 5/369; A61B 5/372; A61B 5/378; A61B 5/4088; A61B 5/6803
See application file for complete search history.

(56) References Cited

U.S. PATENT DOCUMENTS

| 9,131,889 B2 | 9/2015 | Kato et al. | |
| 2003/0013981 A1* | 1/2003 | Gevins | A61B 5/377 |
| | | | 600/544 |

(Continued)

FOREIGN PATENT DOCUMENTS

| JP | 2006-051343 A | 2/2006 |
| JP | 2009-240754 A | 10/2009 |

(Continued)

OTHER PUBLICATIONS

Ji-Yeong Yoon et al., "Relationship Between Cognitive Function and Physical Performance in Older Adults", Japanese Journal of Physical Fitness and Sports Medicine, 2010, No. 59, pp. 313-322, with partial English translation.

(Continued)

*Primary Examiner* — Etsub D Berhanu
(74) *Attorney, Agent, or Firm* — McDermott Will & Emery LLP

(57) ABSTRACT

An electronic device to acquire and analyze electroencephalogram data of the subject includes a cognitive function examination control section that presents examination data used for a cognitive function examination of the subject at the time of executing an operation having a different purpose from that of an electroencephalogram measurement, and a cognitive function analysis section that extracts an index of a cognitive function of the subject from electroencephalogram data of the subject measured when presenting examination data.

5 Claims, 33 Drawing Sheets

(51) Int. Cl.
    *A61B 5/384*     (2021.01)
    *A61B 5/00*     (2006.01)
    *A61B 5/372*     (2021.01)
    *A61B 5/291*     (2021.01)

(52) U.S. Cl.
    CPC ............ *A61B 5/384* (2021.01); *A61B 5/6803* (2013.01); *A61B 5/6815* (2013.01); *A61B 5/742* (2013.01); *A61B 5/749* (2013.01); *A61B 2560/0487* (2013.01)

(56) References Cited

U.S. PATENT DOCUMENTS

| | | |
|---|---|---|
| 2008/0294033 A1 | 11/2008 | Yamazaki |
| 2009/0234216 A1 | 9/2009 | Yanagi et al. |
| 2011/0279676 A1 | 11/2011 | Terada et al. |
| 2015/0305686 A1* | 10/2015 | Coleman .............. A61B 5/7264 600/301 |
| 2017/0188947 A1* | 7/2017 | Connor .................. A61B 5/369 |
| 2018/0078187 A1* | 3/2018 | Anwar .................. A61B 5/369 |

FOREIGN PATENT DOCUMENTS

| | | |
|---|---|---|
| JP | 2009-268826 A | 11/2009 |
| JP | 2012-529939 A | 11/2012 |
| WO | 2010/149157 A1 | 12/2010 |
| WO | 2011/045936 A1 | 3/2013 |

OTHER PUBLICATIONS

International Search Report issued in corresponding International Patent Application No. PCT/JP2017/016991, dated Jun. 13, 2017, with English translation.

\* cited by examiner

FIG. 5A

| PHONE NUMBER [Tel_Num] | NAME [Name] | MAIL ADDRESS [Mail_Address] | RELATION WITH USER [Relation] | NOTIFICATION LEVEL [Information_Level] | PICTURE DATA [Picture_File_No, Validity, Frequency, SInterval, Size] | VOICE DATA [Voice_File_No, Validity, Frequency, SInterval, Volume] | SELECTION SENSORY STIMULUS [Select_Stimulus] |
|---|---|---|---|---|---|---|---|
| 080 999 2222 | machida | Mochi.nhi@xxx.com | SON | ALL NOTIFICATION | [1001,1,0.2,1.5] | [2001,1,0.2,1.5] | P |
| : | : | : | : | : | : | : | |
| 080 988 2111 | harumumoto | harumoto.nr@xxx.com | CARE MANAGER | NOTIFICATION WHEN SIGN IS ACCEPTED | [1007,1,0.2,1.5] | [2007,1,0.2,1.5] | P |

FIG. 5B

| FILE IDENTIFICATION NUMBER [File_ID_No] | STIMULUS TYPE [Stimulus_Type] | DATA VALIDITY [Validity] |
|---|---|---|
| 1101 | P | 1 |
| 2105 | V | 1 |
| 1107 | P | 0 |
| : | : | : |
| 1110 | P | 1 |

RINGTONE SOUNDS OR VIBRATION

ELECTRODE

USER HOLDS SMARTPHONE

COGNITIVE FUNCTION EXAMINATION STARTS WHEN USER TOUCHES ELECTRODES (601)

USER CONFIRMS CALLER WHILE VIEWING SCREEN
(IN CASE OF VISUAL EXAMINATION)

SCREEN EXAMPLE DURING INCOMING CALL

FIG. 10

| EXAMINATION DATA ID No. | FILE NUMBER OF USED IMAGE OR VOICE [Target_File_No, Standard_File_No] | TARGET FREQUENCY [Target_Frequency] | STIMULUS TYPE [Stimulus_Type] | STIMULUS ORDER [Or1,Or2,Or3, Or4,Or5··, OrN] | STIMULUS PRESENTATION INTERVAL [S Int] |
|---|---|---|---|---|---|
| 1 | 1001, 1105 | 0.2 | p | [S,S,S,T,S,S,S,S,S,T,S,S,T] | 1.5 |
| : | | | | | |
| n | 2001, 2003 | 0.1 | v | [S,T,S,S,S,S,S,T,S,S,S,T,S] | 1.5 |

FIG. 12

| ID No. | CALLER (WATCHER) NAME [Name] | STIMULUS TYPE [P] or [V] | MEASUREMENT TIME | | MEASUREMENT DATA (μV, per 5ms) | TARGET: STANDARD FILE NUMBER [Target_File_No, Standard_File_No] | TARGET FREQUENCY [Target_Frequency] | STIMULUS ORDER [Or1,Or2,Or3,Or4,Or5··,OrN] | STIMULUS INTERVAL [SInt] |
|---|---|---|---|---|---|---|---|---|---|
| | | | MEASUREMENT START TIME [Start_Time] | MEASUREMENT END TIME [Start_Time] | | | | | |
| 1 | Mochida | P | 2016/10/01/10/01/03/001 | 2016/10/01/10/01/05/002 | -1.5,-2.0,-4.4,·· | [001,001] | 0.2 | [s,s,t,s,s,s,t,s,s,s,s,s,t] | 1.5 |
| : | : | : | : | : | : | : | : | : | : |
| n | Yodhikawa | V | 2016/12/01/12/01/03/001 | 2016/10/01/10/01/05/002 | -1.5,-2.0,-4.4,· | [001,001] | 0.2 | [t,s,s,s,s,s,t,s,s,s,t,s,t] | 1.5 |

FIG. 13

| ID No. | DATA TYPE [DataType] SelfLog:1, AgeAve:2, ADAgeAve:3 | DATA MEASUREMENT PERIOD WHERE ANALYSIS DATA IS CALCULATED [Start:YYYY-MM-DD, End: YYYY-MM-DD] | PEAK LATENCY TIME OF P300 (AVERAGE) ms | DELAY RATIO (%) FROM AVERAGE PERIOD VALUE OF AVERAGE PEAK LATENCY TIME (%) | PEAK LATENCY TIME ms OF P300 USED IN DETERMINATION OF SIGN PRESENCE OR ABSENCE ms | REQUIRED NUMBER OF SAMPLES |
|---|---|---|---|---|---|---|
| 1 | 1 | [20160701,20160731] | 350 | 15 | 403 | 20 |
| 2 | 2 | 0 | 0 | 0 | 500 | 0 |
| 3 | 3 | 0 | 0 | 0 | 700 | 0 |
| : | : | : | : | : | : | : |

FIG. 14

| ID N O. | DATA CALCULATION PERIOD (START DATE,END DATE) [YYYY-MM-DD, YYYY-MM-DD] | CALLER (WATCHER) [Name] | STIMULUS TYPE [P]or [V] | AVERAGE PEAK LATENCY TIME OF P300(ms) | ANALYSIS DATA TYPE [DataType] SelfLog:1, AgeAve:2, ADAgeAve:3 | SIGN PRESENCE OR ABSENCE DETERMINATION RESULT [Result] PRESENCE:1 ABSENCE:0 |
|---|---|---|---|---|---|---|
| 1 | 2016-11-01,2016-11-30] | hori | V | 380 | 1 | 0 |
| : | : | : | : | : | : | : |
| : | : | : | : | : | : | : |

ALARM SOUNDS OR VIBRATION

USER HOLDS SMARTPHONE

COGNITIVE FUNCTION EXAMINATION STARTS UPON TOUCHING ELECTRODES

USER VIEWS SCREEN FOR TURNING OFF ALARM
DISPLAY IMAGE WITH ICON OF SWITCH OFF AT RANDOM

1901　　SCREEN EXAMPLE WHEN ALARM SOUNDS　　1902
1903

USER TURNS OFF ALARM BY TOUCHING OFF
BUTTON WITH FINGER WHEN PICTURE OF OFF BUTTON
APPEARS WHILE WAITING FOR APPEARANCE
OF OFF BUTTON WITH ATTENTION

ELECTROENCEPHALOGRAPHIC DATA ANALYSIS SYSTEM, INFORMATION PROCESSING TERMINAL, ELECTRONIC DEVICE, AND METHOD OF PRESENTING INFORMATION FOR DEMENTIA EXAMINATION

CROSS REFERENCE TO RELATED APPLICATIONS

This application is the U.S. National Phase under 35 U.S.C. § 371 of International Application No. PCT/JP2017/016991 filed on Apr. 28, 2017, the entire contents is hereby incorporated by reference.

TECHNICAL FIELD

The present invention relates to an electronic device, and more particularly to an electronic device capable of examining a cognitive function using an electroencephalogram technique.

BACKGROUND ART

As a relatively inexpensive brain measurement technique for a dementia examination, there is a near-infrared spectroscopy technique disclosed in Patent Literature 1. Patent Literature 1 discloses that "the technique includes a data acquisition section that acquires biological signal data in a predetermined brain region of a subject measured when giving a task to activate the brain, a feature extraction section that extracts a feature of the biological signal data acquired by the data acquisition section, and a determination section that determines the degree of cognitive impairment of the subject based on the feature extracted by the feature extraction section and data used for determination of the cognitive impairment, which has been obtained in advance".

Moreover, there is a technique disclosed in Patent Literature 2 as an example of an electroencephalographic identification method adjustment device and method using P300. Patent Literature 2 discloses that "a device used for adjusting an identification method of an electroencephalogram interface section includes database that defines a correlation of a P3 component of an event-related potential obtained by stimulus to a modality other than visual and a P3 component of a visual event-related potential, a stimulus presentation section that presents the stimulus through the output section, an analysis section that analyzes the event-related potential contained in an electroencephalogram signal after the stimulus presentation, and an identification method adjustment section that derives the feature of the user related to the P3 component of the visual event-related potential based on the analyzed P3 component of the event-related potential and the database, and adjusts an electroencephalogram identification method in the electroencephalogram interface section based on the feature".

CITATION LIST

Patent Literature

PATENT LITERATURE 1: U.S. Pat. No. 9,131,889
PATENT LITERATURE 2: JP-A No. 2009-268826

SUMMARY OF INVENTION

Technical Problem

In the examination according to Patent Literature 1, there is a need to wear a near-infrared spectroscopic analysis device on the subject. In the examination according to Patent Literature 2, the subject is aware that the subject undergoes a cognitive function examination. Therefore, when performing the examination according to Patent Literatures 1 and 2, there is a concern that a psychological pressure is imposed on the subject to undergo the cognitive function examination.

The present invention has been made in view of the above actual circumstances, and an object of the present invention is to provide a technique which collects data required for a cognitive function examination without imposing a psychological load on a subject.

Solution to Problem

In order to solve the above problems, the present invention has configurations defined in the claims. As an example, the present invention is directed to an electronic device that acquires and analyzes electroencephalographic data of a subject, including a cognitive function examination control section that presents examination data used for a cognitive function examination of the subject at the time of executing an operation having a purpose different from that of an electroencephalographic measurement on the subject, and a cognitive function analysis section that extracts an index of a cognitive function of the subject from the electroencephalographic data of the subject measured when presenting the examination data.

Advantageous Effects of Invention

According to the present invention, there is provided a technique which collects data required for the cognitive function examination without imposing a psychological load on the subject. Problems, configurations, and effects other than those described above will be clarified in the following description of embodiments.

BRIEF DESCRIPTION OF DRAWINGS

FIG. 5A is a diagram of a watcher table configuration.

FIG. 5B is configuration diagram of a standard table.

FIG. 10 is a diagram showing a configuration example of examination data.

FIG. 12 is a diagram showing a data configuration example of electroencephalographic data.

FIG. 13 is a diagram showing a configuration example of analysis data.

FIG. 14 is a diagram showing a data configuration example (average period) of a cognitive function analysis result.

DESCRIPTION OF EMBODIMENTS

Figure 1:
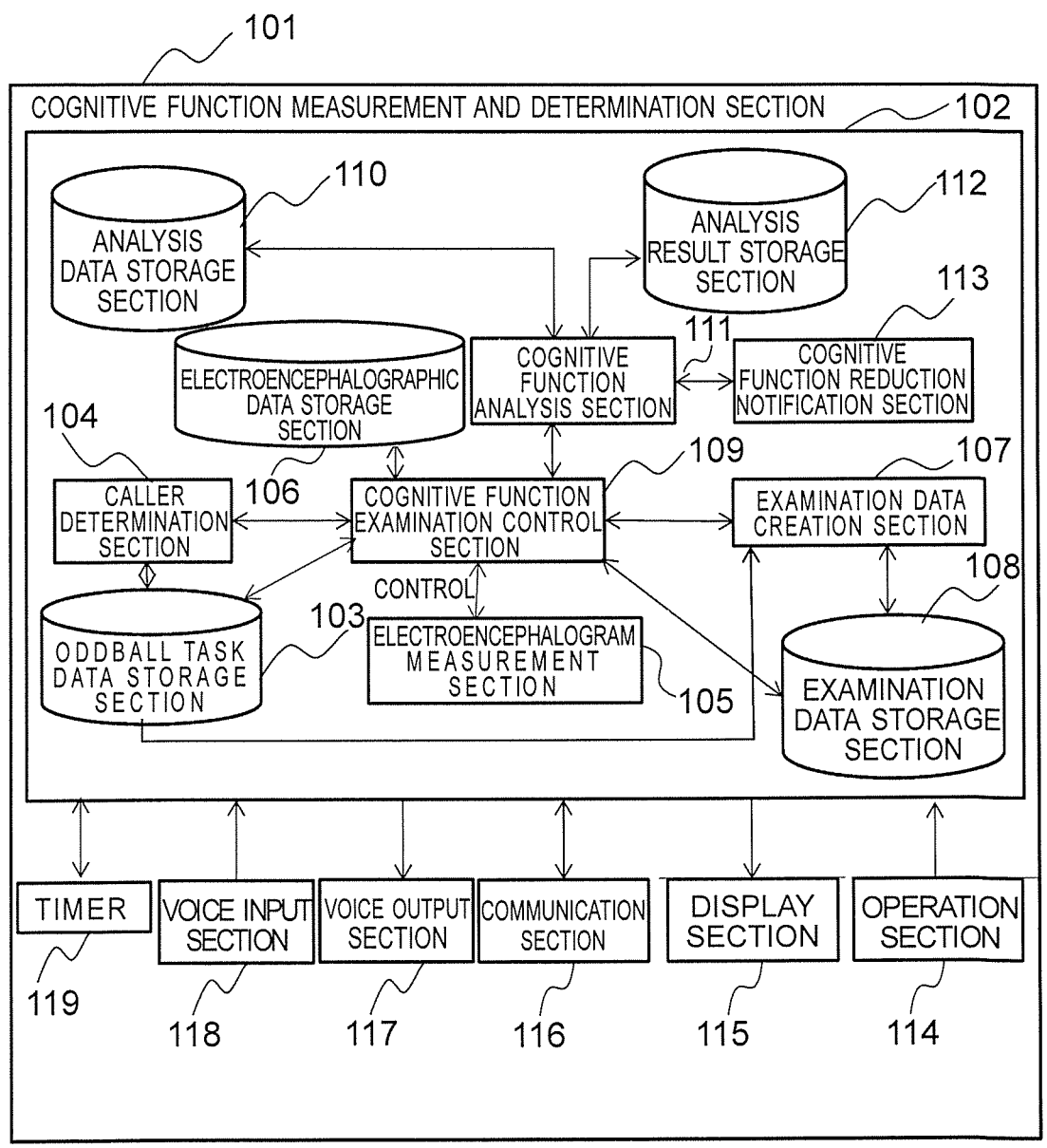
FIG. 1 is a functional block diagram of a cognitive function examination device.

Alzheimer's disease (hereinafter referred to as AD) accounts for about half of dementia. A neurophysiological biomarker such as brain waves is expected to be used as a biomarker for early diagnosis of the AD. The biomarker is a definition of the National Institutes of Health, "an objectively measured and evaluated characteristic as an indicator of normal physiologic, pathological, or pharmacological response to therapeutic intervention".

As compared with brain examination techniques such as fMRI (functional Magnetic Resonance Imaging), a magnetic resonance function imaging method, and an MEG (Magneto Encephalo Graphy), in an electroencephalographical technology, an measurement can be performed with a relatively inexpensive device, and a potential of a head surface is merely measured so that a pressure and restraint on the body at the time of measurement are reduced. As a result, the electroencephalographical technology is expected to be applied to not only a medical field, but also a wide range of fields such as consumer, healthcare, welfare, robots, and in-vehicle.

One of the biomarkers in the electroencephalogram is an event-related potential. The event-related potential is an electrical activity of a brain that occurs temporally in relation to an external or internal event. Potentials related to external events using visual and auditory stimuli are applied to an examination for the AD and a mild cognitive impairment. In particular, a time since a peak latency time stimulus of P300 which is a peak of a third waveform of the event-related potential in a positive direction is presented till P300 appears is leveraged as a biomarker at the time of examining the AD and the mild cognitive impairment. Also, an oddball task is used as a tool to induce the P300. The oddball task is a task in which a subject is presented with two types of stimulus at random, attention is given to stimulus with a low frequency of presentation, and a response such as pressing a button is performed. In the oddball task, a low-frequency stimulus is called a target stimulus (hereinafter referred to as "target"), and a high-frequency stimulus is called a standard stimulus (hereinafter referred to as "standard").

Hereinafter, according to an embodiment of the present invention, an electroencephalographic data analysis system, an information processing terminal, and an electronic device will be described which present an oddball task as information for a dementia examination to a subject at the time of performing an operation having a purpose different from that of the electroencephalogram measurement, and analyze the brains wave of the subject at that time to extract a cognitive function index. In the following description, a smartphone will be mainly described as an example of an electronic device. However, as will be described in each embodiment to be described later, the information processing terminal and the electronic device are not limited to the smartphone. The present invention is similarly applicable to electronic devices such as PCs, tablets, electronic books, home robots, televisions, audio devices such as radios, and electronic devices such as wearable device.

First Embodiment

A first embodiment is an example in which a smartphone is used as an electronic device (hardware) and a cognitive function examination device according to the present invention is implemented into the smartphone.

(Description of Functional Blocks of Cognitive Function Examination Device)

FIG. 1 is a functional block diagram of a cognitive function examination device.

A cognitive function examination device 101 includes a cognitive function measurement and determination section 102, an operation section 114, a display section 115, a communication section 116, a voice output section 117, a voice input section 118, and a timer 119.

The operation section 114 accepts an operation input from a user (corresponding to a subject) to the cognitive function examination device 101 and outputs an operation signal.

The display section 115 performs a control to display an operation screen and various information for the user.

The communication section 116 performs a control to communicate with an external device through various network telephone networks, WiFi, Bluetooth (registered trademark), or the like.

The voice output section 117 and the voice input section 118 perform a voice output and input control through a speaker 225 and a microphone 226 to be described later. The timer 119 generates time information and outputs the time information to the cognitive function measurement and determination section 102.

The cognitive function measurement and determination section 102 includes an oddball task data storage section 103, a caller determination section 104, an electroencephalogram measurement section 105, an electroencephalographic data storage section 106, an examination data creation section 107, an examination data storage section 108, a cognitive function examination control section 109, an analysis data storage section 110, a cognitive function analysis section 111, an analysis result storage section 112, and a cognitive function reduction notification section 113.

The oddball task data storage section 103 stores data for the oddball task. The oddball task data storage section 103 stores, for example, information related to a person (watcher) who watches the user to be subjected to the cognitive function examination, for example, information related to watcher's phone number, name, e-mail address, voice, pictures, and so on.

In the present embodiment, an example in which information related to the watcher is mainly stored in the oddball task data storage section 103 will be described.

When the caller determination section 104 receives a call or e-mail through the communication section 116, the caller determination section 104 determines whether or not a phone partner is a watcher registered in the oddball task data storage section 103.

The electroencephalogram measurement section 105 operates as an electroencephalographic data acquisition section for acquiring electroencephalographic data of the user (subject) to be subjected to the cognitive function examination. The electroencephalogram measurement section 105 includes an electroencephalogram detection sensor for acquiring the electroencephalographic data (in the present embodiment, an electroencephalogram measurement electrode 221 as will be described later).

The electroencephalographic data storage section 106 stores the electroencephalographic data acquired by the electroencephalogram measurement section 105.

The examination data creation section 107 automatically creates data for the cognitive function examination, with the use of the watcher's voice and pictures stored in the oddball task data storage section 103, images such as pictographs and ringtones which are stored in the smartphone in advance, and the like.

The examination data storage section 108 stores the examination data created by the examination data creation section 107.

The cognitive function examination control section 109 detects that a potential is detected from the electroencephalogram measurement electrode 221, which is an electroencephalogram detection sensor in the electroencephalogram measurement section 105 to detect that the electroencephalogram can be detected, starts an examination with the use of the examination data stored in the examination data storage section 108, and stores the measured electroencephalogram in the electroencephalographic data storage section 106. In addition, the cognitive function examination control section 109 executes control of all parts configuring the cognitive function measurement and determination section 102. In this example, the electroencephalogram measurement electrode 221 is used as the electroencephalogram detection sensor, but a magnetic sensor may be used.

The analysis data storage section 110 stores data for analyzing and evaluating the cognitive function.

The cognitive function analysis section 111 analyzes the electroencephalographic data stored in the electroencephalographic data storage section 106, and compares the analyzed electroencephalographic data with data in the analysis data storage section 110, which is calculated in advance, to thereby perform the cognitive function analysis.

The analysis result storage section 112 stores the analysis result of the cognitive function analysis section 111.

When the reduction of the cognitive function is detected and a sign of dementia is detected in the cognitive function analysis section 111 (corresponding to a case in which a predetermined notification criterion is satisfied), the cognitive function reduction notification section 113 notifies a watcher registered in advance in the oddball task data storage section 103 of this fact.

The watcher who is registered in the oddball task data storage section 103 is directed to a watcher who casually watches the life and health of a user elderly to be subjected to the cognitive function examination, and for example, a user's family or a care manager. If the watcher uses a smartphone to which the cognitive function examination device 101 is applied, the watcher can watch a state of the cognitive function in a daily life of the elderly user even from a remote location.

The data to be registered in the oddball task data storage section 103 may be a data phone number, a name, an address, an e-mail address, and so on of an existing address book of the smartphone, a picture, a data phone number, a name, an e-mail address, and voice stored in an internal memory or a SD card, or may be registered with the use of data newly sent from the watcher.

(Description of Hardware Configuration)

Figure 2:
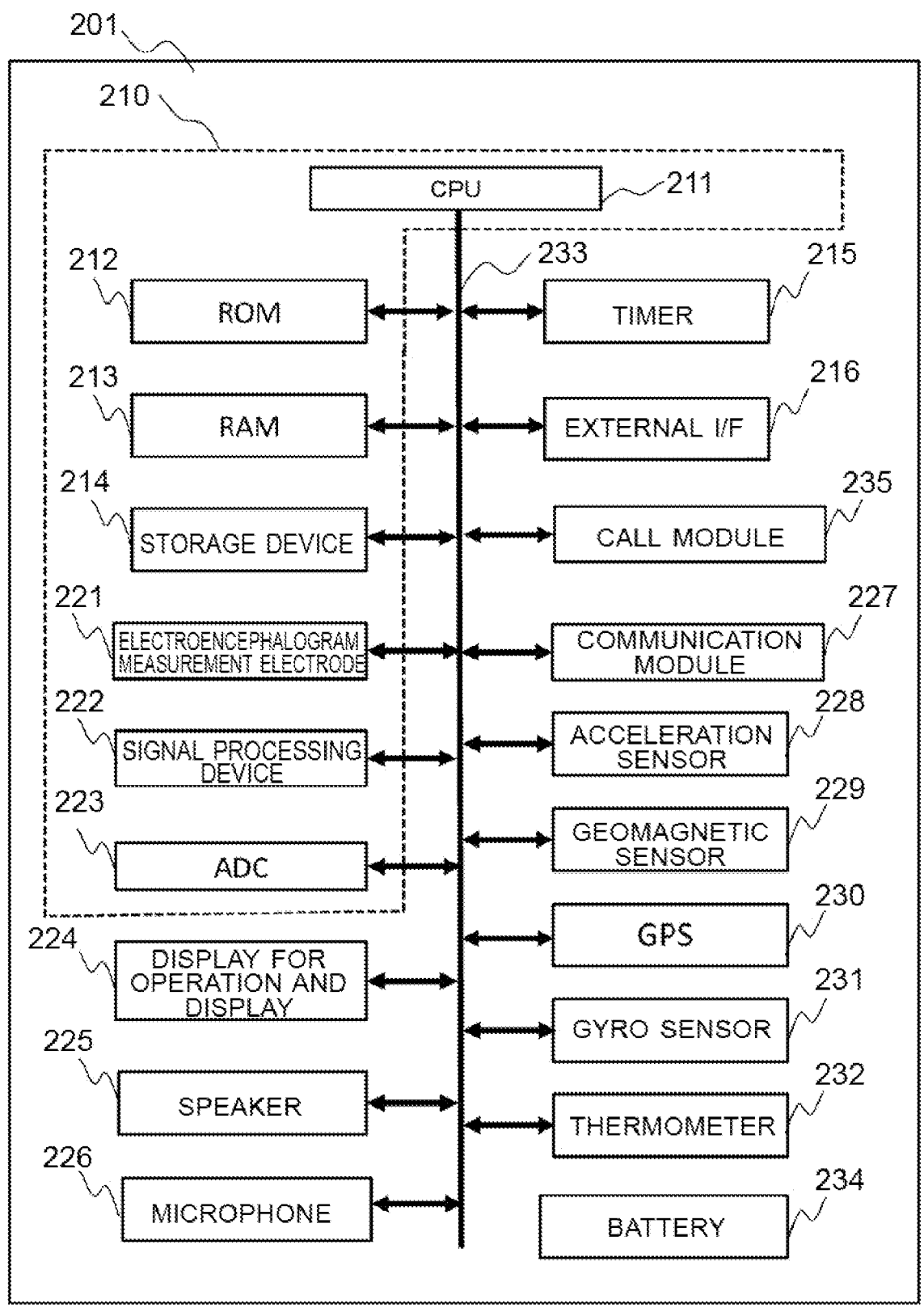
FIG. 2 is a hardware configuration diagram of a cognitive function examination device smartphone.

FIG. 2 is a diagram showing a hardware configuration of a smartphone to which the cognitive function examination device 101 described in FIG. 1 is applied.

A smartphone 201 includes a CPU (Central Processing Unit) 211 that controls the entire system of the smartphone 201, a ROM (Read Only Memory) 212 that stores a basic program such as an OS to be used in the smartphone, a RAM (Random Access Memory) 213 that temporarily stores programs and various pieces of data, and used as a cache and a work memory, a storage device 214 that stores the programs for realizing the functions of the cognitive function examination device 101, various pieces of data used in the respective functional blocks, and the measurement result of electroencephalogram, a timer 215 (corresponding to the timer 119 in FIG. 1) used for acquiring a time at electroencephalogram measurement, timer setting, and an external I/F 216 connected to an external device. In this example, the storage device 214 is configured by a nonvolatile memory such as an HDD (Hard Disk Drive) or a flash memory. In this example, since the cognitive function examination device 101 according to the present embodiment is applied to a smartphone, it is preferable that the storage device 214 is configured by a nonvolatile memory. In addition, when the cognitive function examination device 101 according to the present invention is applied to a PC, the storage device 214 is configured by an SSD (Solid State Drive) having an HDD or a flash memory.

Furthermore, the smartphone 201 includes an electroencephalogram measurement electrode 221 for measuring a potential of the electroencephalogram, a signal processing device 222 that removes noise derived from the electroencephalogram measurement electrode 221 and amplifies a signal from which the noise has been removed, an ADC (analog to digital converter) 223 that converts an analog signal processed by the signal processing device 222 into a digital signal, a display 224 for operation and display (corresponding to the operation section 114 and the display section 115 in FIG. 1) that includes a touch panel (not shown) for receiving or inputting user's operation and displays an image and providing the image to the user, a speaker 225 (corresponding to the voice output section 117 in FIG. 1) for reproducing a ring tone and voice, a microphone 226 (corresponding to the voice input section 118 in FIG. 1) that receives voice, a wired or wireless communication module 227 (corresponding to the communication section 116 in FIG. 1) for communicating with external devices, an acceleration sensor 228 that detects data related to tilt, movement, vibration and impact, a geomagnetic sensor 229 for measuring an azimuth, a GPS (Global Positioning System) 230 for acquiring position information of a receiver, a gyro sensor 231 that detects a change in rotation or orientation, a thermometer 232 for measuring a body temperature, a system bus 233 that is a data communication path for transmitting and receiving data between the CPU 211 and each component of the smartphone 201, a battery 234 for supplying an electricity, and a call module 235.

The communication module 227 includes a wireless communication function such as 3G and 4G, Wi-Fi, Bluetooth, an infrared communication, a broadcast service communication and a wired communication function such as a wired LAN.

In this example, among the respective functional blocks shown in FIG. 1, the electroencephalogram measurement electrode 221, the signal processing device 222, the ADC 223, the CPU 211, the ROM 212, the RAM 213, and the storage device 214 are hardware 210 configuring the cognitive function measurement and determination section 102. The hardware 210 and a program for realizing the cognitive function measurement and determination function cooperate with each other to configure each functional block of the cognitive function measurement and determination section 102 shown in FIG. 1.

(Example of Mounting Electroencephalogram Measurement Electrode on Smartphone)

Next, an example of mounting the electroencephalogram measurement electrode 221 on the smartphone 201 will be described with reference to FIG. 3.

In general, an electroencephalogram is derived from an electrode placed on a scalp and measured. In recent years, a technique for reading the electroencephalogram from a skin surface of an arm or a hand, such as a body wave technology, has been developed. For that reason, an example in which the electroencephalogram measurement electrode 221 is mounted by leveraging the above technique is illustrated in FIG. 3A and FIG. 3B.

Figure 3A:
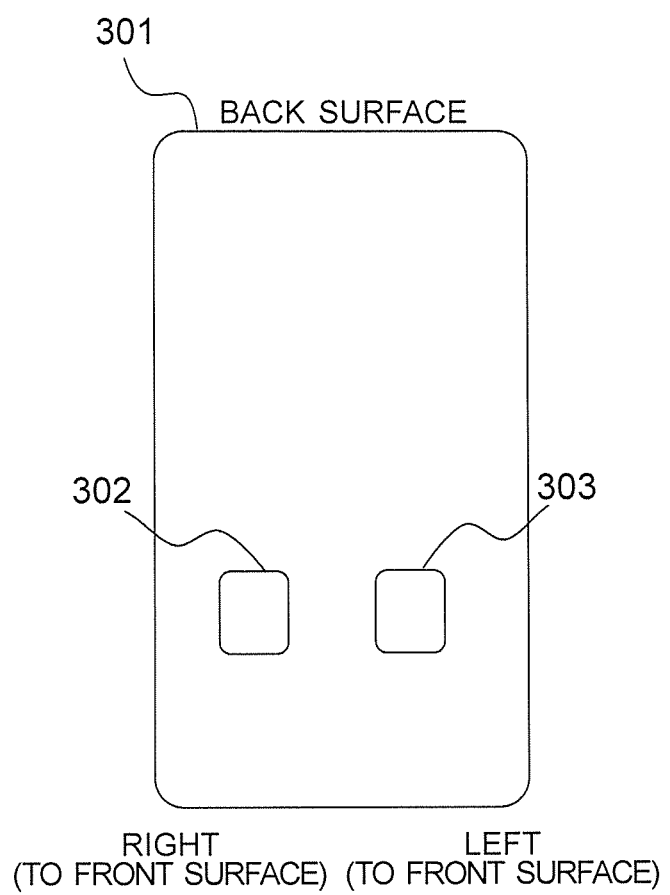
FIG. 3A is a rear view showing a mounting example of the cognitive function examination device smartphone.

FIG. 3A shows an example in which bipolar electroencephalogram measurement electrodes 302 and 303 are disposed on a back surface 301 of the smartphone 201. An induction method is bipolar induction, and an electroencephalogram is measured by a potential difference derived from two electrodes. The electrodes are placed in portions of the back surface where a hand easily touches. In FIG. 3A, two electrodes are mounted, but two or more electrodes may be placed, and measurement may be performed by automatically selecting two portions touched by the hand.

Figure 3B:
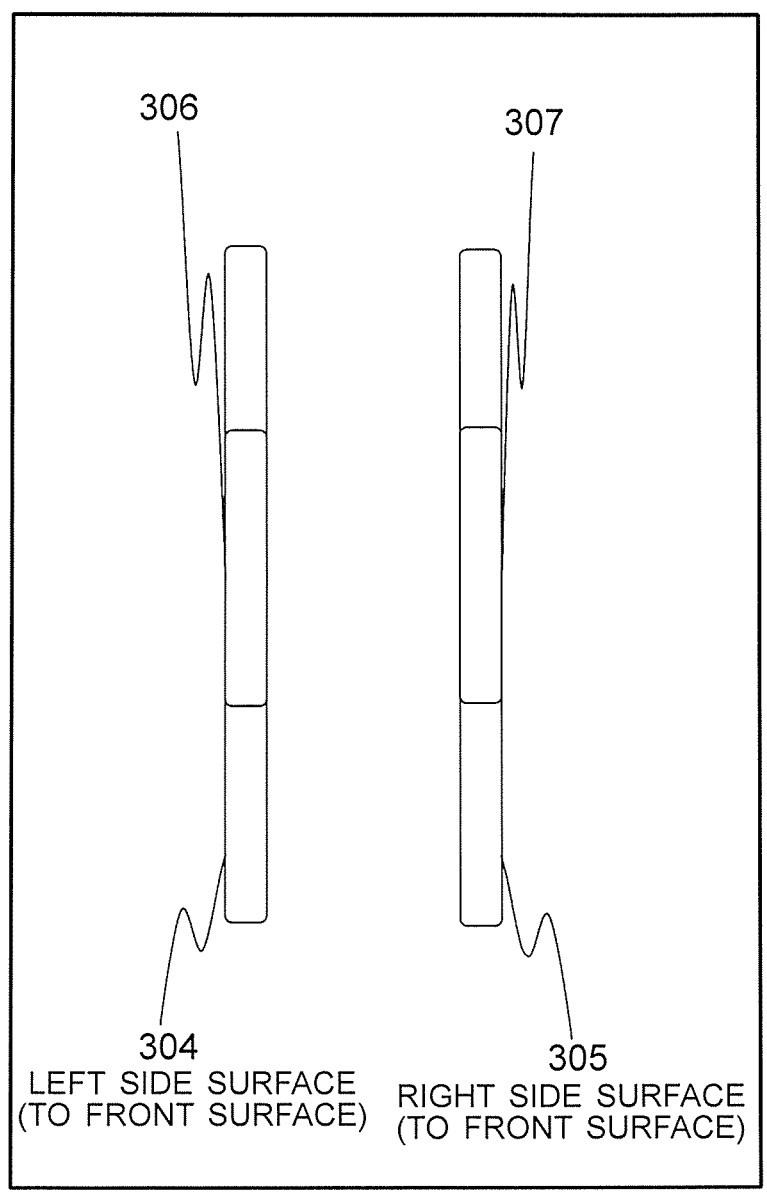
FIG. 3B is a side view showing the mounting example of the cognitive function examination device smartphone.

FIG. 3B is an example in which the electroencephalogram measurement electrodes 306 and 307 are placed on a left-side surface 304 relative to a front surface of the smartphone and a right-side surface 305 relative to the front surface, respectively.

As in FIG. 3A, the electrodes are disposed by bipolar induction. When gripping the smartphone, the electroencephalogram is measured by a potential difference derived from two positions of a surface of the hand. Two or more electrodes may be placed, and with the potential detected by touching the electrodes with the hand, it may be detected that the hand has touched the electrodes, and two electrodes touched by the hand may be automatically selected and measured.

In this example, both of the electrodes shown in FIGS. 3A and 3B may be mounted, or a combination of those electrodes may be used. For example, an electrode may be disposed at one place on the back surface and one electrode may be disposed at one place on a side surface, or an electrode may be disposed at one place on the back surface and two electrodes may be disposed at two places on the side surface in a mixed manner.

Figure 3C:
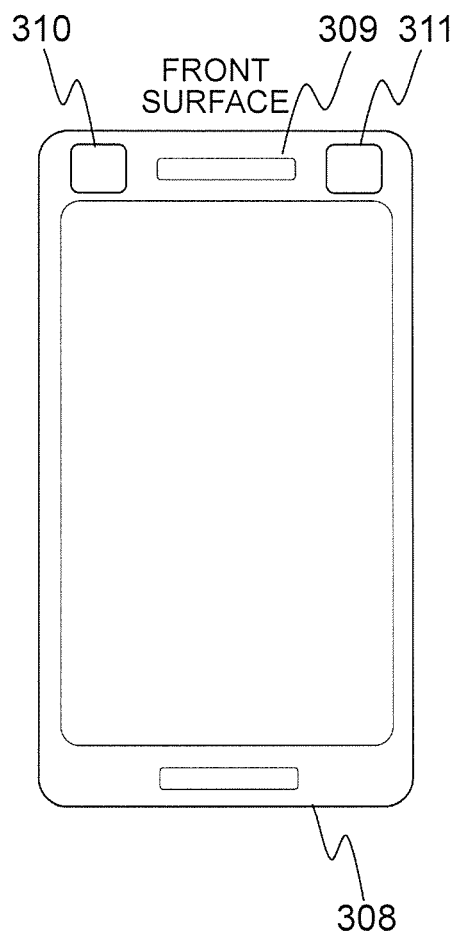
FIG. 3C is a front view showing the mounting example of the cognitive function examination device smartphone.

FIG. 3C shows a placement of electrodes when the electrodes capable of detecting a potential in a non-contact state are used. Electrodes 310 and 311 are placed in the vicinity of a speaker 309 on a front surface 308 of the smartphone. In recent years, non-contact electrodes for a body area network have been developed. For that reason, an example of an electrode placement in the case of using the above technology is shown. When an incoming call is received, the potential can be derived by bringing the speaker 309 on the front surface 308 of the smartphone closer to an ear. With the provision of the non-contact electrodes, there is no need to bring the electrodes in contact with a head. The electrodes 310 and 311 are each provided with an amplifier ADC and a communication module, and the derived potential can be transmitted from one electrode to the other electrode. With the above electrodes, the potential can be derived even if there is an insulator between the electrodes and the head.

In this example, all of the electrodes of FIGS. 3A, 3B, and 3C may be mounted, or a configuration in which the electrodes shown in FIGS. 3A, 3B, and 3C are mixed together may be used. For example, the combination of FIG. 3C with FIG. 3B or FIG. 3C with FIG. 3A may be used.

(Description of Basic Waveform of Electroencephalogram and Event-Related Potential, and Features of P300).

Figure 4:
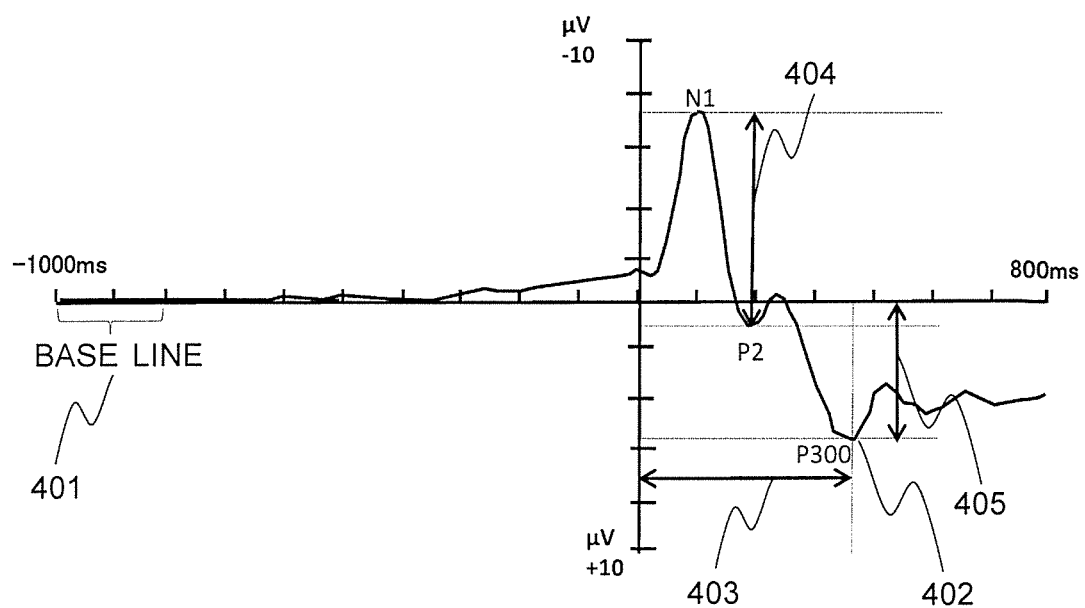
FIG. 4 is a graph of a basic waveform of an event-related potential.

Next, the electroencephalogram data acquired in the present embodiment will be described with reference to FIG. 4. Originally, the electroencephalogram is obtained by recoding an electrical activity of the neuron of brains, and a change in the potential derived from the electrodes attached to a scalp is mainly recoded as a waveform over time. There are two types of electroencephalograms of a spontaneous electroencephalogram and an induced electroencephalogram. The spontaneous electroencephalogram is a potential that is constantly fluctuating regardless of the occurrence of a specific event, and is an electroencephalogram in a continuous state. On the other hand, the induced electroencephalogram is a potential (hereinafter referred to as an event-related potential) occurring in relation to the occurrence of an event. The induced electroencephalograms include an extrinsic type originating from perceptual vision, hearing, and somatic sense, and an intrinsic type related to mental events such as expectation, attention, and decision making. In this example, a basic waveform of the event-related potential of the electroencephalogram will be described briefly with reference to FIG. 4 will be briefly described. FIG. 4 is an illustrative diagram showing the basic waveform of the event-related potential of the electroencephalogram.

The event-related potential is represented with a vertical axis as a potential "μV" and a horizontal axis as a time "ms". In many cases, the waveform of the event-related potential is expressed as a negative on an upper side and a positive on a lower side. A point of the event occurrence is indicated by 0 "ms" on the horizontal axis on the graph in the case of an external stimulus. The waveform near 0 μV is called a baseline 401. In a negative direction of the electroencephalogram, an upward reflection is called N (Negative), and in the positive direction, a downward reflection is called P (Positive), and numbers are added in the order of occurrence of each waveform (P1, P2, and so on in the figure). Alternatively, waveforms are distinguished from each other with a standard peak latency time in "ms" unit. The peak latency time is a time till the appearance of a peak after receiving a stimulus.

P300 (reference numeral 402) induced by the oddball task described above is an apex of a third waveform in the positive direction, and since the peak latency time is about 300 ms, the apex is also called P300. When analyzing the feature of the electroencephalogram, in addition to the peak latency time, an amplitude 404 between the vertices and a peak amplitude value 405 based on a base line are also used.

A peak latency time 403 of P300 has been known as a biomarker of the AD. It has been known that the peak latency time 403 of P300 (reference numeral 402) is generally delayed with aging, but is further delayed in AD patients compared with the peak latency time with aging. In addition, it has been known that the reduction of the cognitive function becomes stronger as the peak latency time is delayed in the AD patients. In addition, it has been known that the peak latency time 403 of P300 (reference numeral 402) is delayed even in healthy individuals who have a genetically high risk of AD.

In the oddball task, in providing stimulus such as a plurality of images and voice to the user, a stimulus presented at a low frequency is called a target, and a stimulus presented at a high frequency is called a standard.

It has been known that P300 (reference numeral 402) is lowered in the frequency of appearance when the frequency of the target becomes relatively high in the presented stimulus, and P300 is likely to appear when the frequency of the target is low. Since there are individual differences in the appearance situation of P300 (reference numeral 402) with respect to those target frequencies, there is a need to adjust the target frequency (frequency of presenting the target to the user) according to the characteristics of each person.

Further, P300 (reference numeral 402) may not appear when attention to the target during execution of the oddball task is reduced, and maintenance of attention to the target at the time of task execution is also important.

Further, the peak latency time 403 of P300 is often calculated mainly by averaging the event-related potentials. This is because the induced electroencephalogram also contains spontaneous electroencephalogram components, and those components are generated randomly. The peak latency time 403 is frequently obtained by mainly averaging the event-related potentials in order to remove the effects of the spontaneous electroencephalogram. However, since there is a method of calculating the peak latency time 403 of P300 (reference numeral 402) from one event-related potential, the calculation method is not limited to the averaging.

In the present embodiment, the oddball task for causing the P300 (reference numeral 402) to appear is presented to the subject when performing an operation having a purpose different from that of the electroencephalograph measurement, for example, an operation for answering an incoming call, and an examination for causing P300 (reference numeral 402) to appear is performed without giving the subject a mental burden due to imposing a cognitive function examination on the subject. Hereinafter, data used for this purpose will be described.

(Configuration Example of Watcher Table)

Next, the configuration of a table 501 (hereinafter referred to as "watcher table") when data relating to the watcher is stored in the oddball task data storage section will be described with reference to FIG. 5A.

The watcher table 501 includes a watcher's phone number 502 [Tel_Num], name 503 [Name], e-mail address 504 [Mail_Address], a relation with the user 505 [Relation], contact level data 506 [Information_Level], a picture data item 507, a voice data item 508, and a selection sensory stimulus 517 [Select_Stimulus].

The relation 505 with the user describes data indicating the relation with the user, for example, information on a family relation (son or daughter), a person in charge of a watching service such as a care manager or an associated doctor.

The contact level data 506 stores a notification level such as the analysis result of the measurement result. For example, in the case of a family member, the notification level may be set to notify the family member of the analysis result every time the result is obtained, and in the case of a person concerned such as the care manager, the notification level may be set to notify the person concerned of the analysis result only when the sign has been detected.

The picture data item 507 holds data of a file number 509 [Picture_File_No] of a file storing the watcher's picture, a variable 510 [Validity] indicating whether or not P300 has been detected in an initial test to be described later, a presentation frequency 511 [Frequency] in the oddball task (stored based on the result of the initial test, 20% or less is a guideline), an interval 512 [SInterval] at which to display pictures (stored based on the result of the initial test, a unit is "ms", 1.5 ms is a guideline), and a picture size 518 [Size] to be displayed in the oddball task.

Similarly, the voice data item 508 holds data of number 513 [Voice_File_No] of a file storing the voice of the watcher, a variable 514 [validity] indicating whether or not P300 has been detected in the initial test to be described later, a presentation frequency 515 [Frequency] in the oddball task (stored based on the result of the initial test, 20% or less is a guideline), an interval 516 [SInterval] at which to reproduce the voice (stored based on the result of the initial test, a unit is "ms", 1.5 ms is a guideline), and a volume 519 [Volume] for reproducing the voice in the oddball task.

The selection sensory stimulus 517 holds the sensory stimulus when the cognitive function examination is performed. In an example of FIG. 5A, "P" is input when a visual picture is selected, and "V" is input when an auditory voice is selected.

The same selection sensory stimulus 517 is applied to any watcher after selection.

The sense to be used in the examination is set by the user as a sensory stimulus (image, voice, or vibration) to be preferentially used as an interface with the smartphone at the start of use of the cognitive function examination device, or by a method of a second embodiment to be described later.

Figure 7:
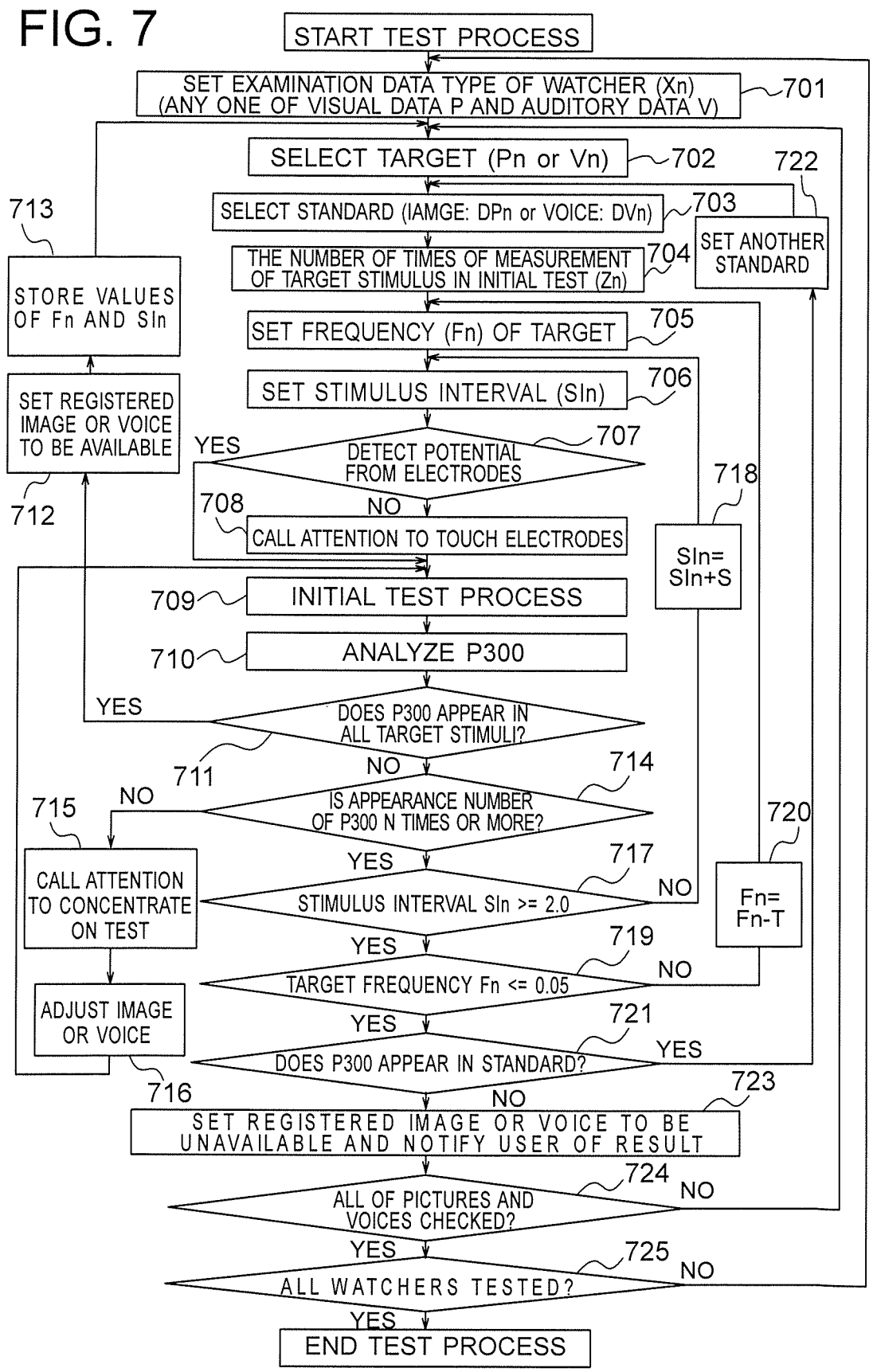
FIG. 7 is a flowchart of an initial setting test for creating examination data.

When this process is performed at the start of use of the cognitive function examination device, the process is performed immediately after executing an initial setting flow of FIG. 7. However, the process can be changed even after that time.

(Configuration Example of Standard Table)

Next, a configuration of a table 520 (hereinafter referred to as "standard table") that stores standard data in the oddball task data storage section 103 will be described with reference to FIG. 5B.

The standard table 520 stores data related to standards used in oddball tasks. The standard table 520 includes a file identification number 521 [File_ID_No], a stimulus type 522 [Stimulus_Type], and data validity 523 [Validity].

The file identification number 521 is an identification number of the file of picture data and voice data which is a standard.

The stimulus type 522 indicates the type of stimulus to be presented to the user, and is set to "P" when the type is image data which is a visual stimulus, and set to "V" indicative of auditory data when the type is voice data which is an auditory stimulus.

The data validity 523 [Validity] is set to "1" if data can be used as a standard without any problems during the initial test, which will be described later, and set to "0" if data is not suitable for use due to the appearance of P300 that should not originally occur.

(Description of how to Use Smartphone Equipped with Cognitive Function Examination Device at the Time of Receiving Incoming Call)

Next, how to use the smartphone equipped with the cognitive function examination device 101 according to the present invention at the time of receiving incoming call is described with reference to FIG. 6.

An example of the smartphone 201 in which the electroencephalogram measurement electrodes 302 and 303 are disposed on the back surface shown in FIG. 3A will be described with reference to FIG. 6.

Figure 6A:
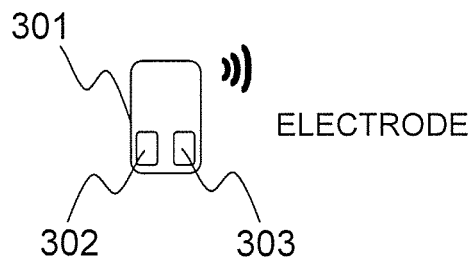
FIG. 6A is a diagram illustrates an example of how to use the smartphone at the time of incoming (incoming call).
Figure 6B:
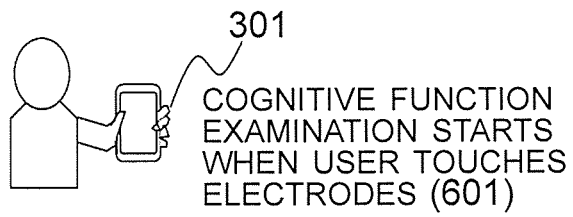
FIG. 6B is a diagram illustrates an example of how to use the smartphone at the time of incoming (held state).

When a call is received from the watcher registered in the watcher table on the smartphone 201, the smartphone 201 notifies the incoming call by a ringtone or vibration (FIG. 6A). When the user holds smartphone 201 and brings a surface of his or her hand in contact with the two electroencephalogram measurement electrodes 302 and 303 on the back surface 301 of the smartphone 201, the smartphone 201 starts a cognitive function examination (FIG. 6B, reference numeral 601).

Figure 6C:
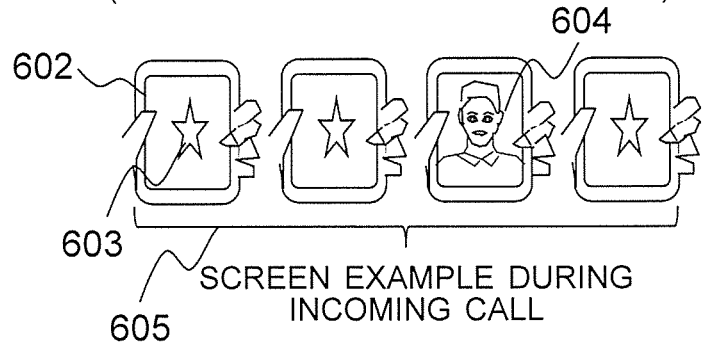
FIG. 6C is a diagram illustrates an example of how to use the smartphone at the time of incoming (visual stimulus).

When the cognitive function examination is set as "visual examination", that is, when a value of the selection sensory stimulus 517 [Select_Stimulus] in the watcher table 501 is set to "P", the user confirms a caller by looking at the screen (FIG. 6C).

In other words, an image 603 such as a pictogram selected as the standard, and a face picture (corresponding to a face image) 604 of the caller, who is a target, are displayed on the screen 602 of the smartphone at random.

The user confirms the caller by looking at the face picture 604 displayed on the screen 602 from a series of images 605 displayed.

Figure 6D:
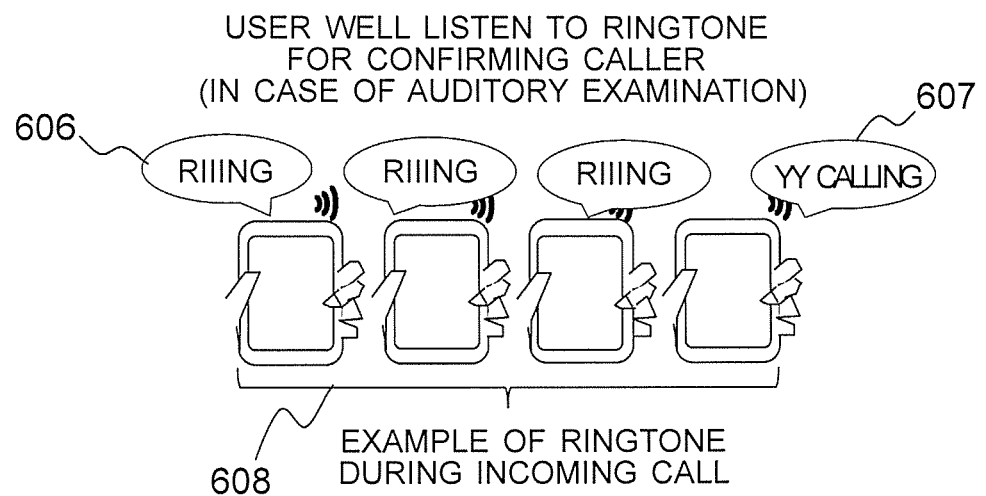
FIG. 6D is a diagram illustrates an example of how to use the smartphone at the time of incoming (auditory stimulus).

On the other hand, when the cognitive function examination is set to "examination by auditory sense", the value of the selection sensory stimulus 517 [Select_Stimulus] in the watcher table 501 is set to "V". In that case, the user confirms the caller by listening to the ringing tone (FIG. 6D). In other words, when the user brings the surface of his hand into contact with the electroencephalogram measurement electrodes 302 and 303 on the back surface 301 of the smartphone, a ringtone 606 and a reading voice 607 of the name based on the caller's voice are reproduced at random. The user confirms the caller by listening to a series of ringing voices 608.

The user confirms who is the caller is based on the caller's face picture 604 or the reading voice 607 of the name, and then presses a reception button to start a call.

The standard voice to be used in the oddball task may be a call which is previously stored in the smartphone, or may be obtained by selecting any voice from the ringtones stored by the user.

(Flow of Initial Setting Test)

A test flow at the time of initial setting will be described with reference to FIG. 7. FIG. 7 is a test flowchart at the time of initial setting. This flow is a process flow at the time of initial setting when starting to use the cognitive function examination device 101 according to the present invention.

The purpose of this test flow is to select data of the standard and the target and confirm whether or not the data can be used for the user's cognitive function examination.

Factors affecting the examination include a suitability of both stimulus data (standard and target) as data, a frequency of the target in the examination, an interval at which the target and the standard are presented to the user, a quality of the stimulus (image size and voice volume), and so on. This test flow serves to set and adjust those elements appropriately.

This initial setting test flow is performed by the cognitive function examination control section 109.

Upon confirmation that the examination is properly executed in the test flow, the cognitive function examination control section 109 stores a validity of the target used in the test in a Validity 510 of a picture data item 507 or in a Validity 514 of the voice data item 508 in the watcher table.

Also, the result of this test process flow is stored in the picture data item 507 and the voice data item 508 of the watcher table 501.

The watcher table 501 and the standard table 520 are used for the examination data creation section 107 to create the examination data.

Further, the examination data created by the examination data creation section 107 is used when the cognitive function examination control section 109 performs the examination.

In this test flow, it is assumed that data related to the watcher of the watcher table 501 has been set by the user in advance.

The above process is executed by, for example, displaying a watcher registration screen or the like for the user before executing this test flow and using the member's phone number, e-mail address, picture, and so on registered in advance in a smartphone's phone book, and so on, and selecting the watcher from the registered data. The selected result is registered in the phone number 502, the name 503, the mail address 504, and the relation 505 with the user in FIG. 5A. Hereinafter, the test flow at the time of initial setting will be described in detail.

In a flow of FIG. 7, visual data and auditory data are assumed as the types of the examination data. However, in addition to the above data, there is a stimulus data for somatosensory, such as vibration as the type of examination data, but the type of the examination data is not limited to those types of data.

First, the cognitive function examination control section 109 selects one watcher (Xn) from the watcher table 501 and selects a picture data item 507 (visual data P) or a voice data item 508 (auditory data V) (Step 701).

Next, the cognitive function examination control section 109 selects one image or voice from the visual data P or the auditory data V selected in Step 701 (Step 702). In the case of the visual data, the cognitive function examination control section 109 selects the picture data 509 [Picture_File_No] stored in the watcher table 501, and in the case of the auditory data, the cognitive function examination control section 109 selects the voice data 513 [Voice_File_No] stored in the watcher table 501.

Next, the cognitive function examination control section 109 selects the standard from pictograms, icons, ringtones, and the like registered in advance in the smartphone or the like (Step 703). In the case of the visual data, the cognitive function examination control section 109 selects pictograms and icons DPn, and in the case of auditory data, the cognitive function examination control section 109 selects incoming data DVn.

Then, the cognitive function examination control section 109 sets an initial value of a target stimulus measurement number Zn in the initial test (Step 704). The number of target stimuli is set a plurality of times, for example, 3 times, in order to confirm the reproducibility of a response to the stimuli. Also, the initial value=<Zn, for example, 2 times is set as the number of appearances N of P300.

Next, the cognitive function examination control section 109 sets an initial value of the target frequency Fn (Step 705). The target frequency is generally about 20%, and, for example, when five images are prepared, the cognitive function examination control section 109 sets one of those images as an image for target stimulus. In general, as the frequency of stimulus to which attention is paid, at which the target is presented to the frequent user is lower, P300 is likely to appear. Since there are individual differences in how to respond to the stimulus of P300, the test is started from 20%, and if P300 does not appears well, the frequency is lowered than 20%.

Next, the cognitive function examination control section 109 sets an initial value of a stimulus interval SIn for presenting the stimulus to the user (Step 706). The stimulus interval is an interval at which the stimuli of the target and standard are presented to the user. In the oddball task, a time of the stimulus interval between the standard and the target, which is presented to the user, is 1.5 s as a guideline. This interval also needs to be adjusted because the response to the stimulus varies from person to person.

Next, the cognitive function examination control section 109 uses the electroencephalogram measurement section 105 to check whether or not the potential has been detected from the electroencephalogram measurement electrodes 302 and 303 on the back surface of the smartphone (Step 707), and if the potential has not been detected from the electrodes ("NO" in Step 707), the cognitive function examination control section 109 calls attention to the user so as to come in contact with the electroencephalogram measurement electrodes 302 and 303 (Step 708). As a method of calling attention, in the case of the examination using an image, the cognitive function examination control section 109 calls attention to the user on a screen of the smartphone, and in the case of the examination using voice, the cognitive function examination control section 109 calls attention to the user with voice through the speaker 225 of the smartphone.

If the potential has been detected from the electrodes ("YES" in Step 707), the cognitive function examination control section 109 starts an initial test (Step 709).

The initial test process (Step 709) is a test for executing an examination for test with the use of the standard and target selected in Steps 702 and 703, the set target stimulus measurement count, the target frequency, and the stimulus interval. Specifically, a series of operations as illustrated in FIGS. 6A to 6C are performed in a pseudo manner.

Next, the cognitive function examination control section 109 performs an analysis of P300 with the use of the electroencephalogram data measured in the initial test process (Step 709) (Step 710).

The cognitive function examination control section 109 temporarily stores the waveform for each target stimulus during the test execution and the analysis result of P300 (whether the waveform is generated) in the buffer RAM 213.

If P300 appears from the user for all the target stimuli in the test ("YES" in Step 711), the cognitive function examination control section 109 sets the image or voice registered in the watcher table 501 to be available (Step 712). Specifically, the cognitive function examination control section 109 sets a value of the Validity variable 510 or 514 of the watcher table 501 to 1. A value 1 of the Validity variable 510 or 514 means that the image or voice is available.

Then, the cognitive function examination control section 109 stores the target frequency Fn (set in Step 705), the stimulus interval SIn (set in Step 706), the size of the picture, and the value of the volume for reproducing the voice, as the presentation frequency [Frequency] variable 511 or 515 that is the target attribute of the watcher table 501, [SInterval] variable 512 or 516, the variable of the picture size 518 [Size], and the variable of the volume 519 [Volume] (Step 713).

As the values of the variables of the picture size 518 [Size] and the volume 519 [Volume], initial setting values or values after adjustment in Step 716 are input.

Finally, data on the standard used in the test is stored in the standard table 520. That is, the standard file number is stored in the file identification number [File_ID_No] of the standard table, and the standard data type is stored in the stimulus type [Stimulus_Type] 522 of the standard table 520 (if the standard is image data, "p" is input, and the standard is voice data, "v" is input), and "1" is input in the data validity [Validity] 523.

Next, another registered image or voice is selected (Step 702).

In Step 711, when P300 does not appear from the user for all the target stimuli ("NO" in Step 711), it is checked whether or not P300 appears N times or more ("NO" in Step 714). If P300 does not appear ("NO" in Step 714), attention is called to concentrate on the test (Step 715). Since P300 may not appear due to distraction, P300 has a Step for prompting such attention. Thereafter, the size or volume of the image or voice is adjusted (Step 716), and the initial test is executed again (Step 709).

In Step 714, when the appearance of P300 with respect to the target stimulus can be confirmed N times ("YES" in Step 717), the cognitive function examination control section 109 determines whether or not the stimulus interval SIn=>2.0 is met (Step 717), and if SIn=>2.0 is not met ("NO" in Step 717), the stimulus interval SIn is increased by S (Step 718). The variable S is set to 0.1, for example.

In Step 717, if the stimulus interval SIn=>2.0 is met ("YES" in Step 717), the cognitive function examination control section 109 determines whether or not the target frequency<=0.05 is met at that time (Step 719). If the target frequency<=0.05 is not met ("NO" in Step 719), the target frequency is reduced by T (Step 720). For example, the variable T is set to −0.05%, for example.

In Step 719, when the target frequency<=0.05 is met ("YES" in Step 719), the cognitive function examination control section 109 determines whether or not P300 appears with respect to the standard (Step 721). If P300 appears ("YES" in Step 721), the cognitive function examination control section 109 selects a pictograph, an icon, or a ringtone in which another image or voice is stored in advance in the smartphone (Step 722), and the process returns to Step 703.

Normally, the waveform of P300 does not appear in the standard, but since it cannot be said that P300 does not appear in the target due to the stimulus of the standard, the waveform of the electroencephalogram in the standard is finally confirmed.

If P300 does not appear in the standard ("NO" in Step 721), the cognitive function examination control section 109 sets the registered image or voice to be not available and notifies the user of the result (Step 723).

Specifically, the cognitive function examination control section 109 sets the value of the Validity variable 510 or 514 of the watcher table 501 to 0. A value "0" of the Validity variable 510 or 514 means that the registered image or voice is unavailable.

The reason for notifying the user is to notify that the registered watcher data is not appropriate for the examination. Upon receiving this notification, the user needs to newly register data for the watcher. The result notification includes the contents.

It is checked whether or not all the pictures and voices have been checked (Step 724). If not checked ("NO" in Step 724), the process returns to Step 702 to select a new target.

If all the pictures and voices have been checked ("YES" in Step 724), it is checked whether all the watchers have been tested (Step 725), and if not tested ("NO" in Step 725), the process returns to Step 701 to select another watcher. If all the watchers have been tested ("YES" in Step 725), the test process is terminated.

In this example, in Step 717, a boundary value of SIn is set to 2.0, but the present invention is not limited to this value.

When P300 appears in the standard in Step 721, the file number of the data used as the standard is input to the file identification number 521 [File_ID_No] of the standard table 520, and "p" is input to the stimulus type [Stimulus_Type] 522 of the standard table 520 if the standard is image data, and "v" is input to the stimulus type [Stimulus_Type] 522 if the standard is voice data.

Also, "0" is input to the data availability [Validity] 523 of the standard table 520.

(Configuration Example of Examination Data (Table))

FIG. 10 is a configuration example of the examination data table stored in the examination data storage section 108.

The table 1001 (hereinafter referred to as "examination data storage table") of the examination data storage section 108 includes examination data ID No. 1002, a used image or voice file number 1003, a target frequency 1004 [Target_Frequency], and a stimulus type 1005 [Stimulus_Type], the stimulus order 1006 [Or1, Or2, Or3, Or4, Or5, . . . OrN] of the visual stimulus P or auditory stimulus V, and the target and standard order and stimulus presentation interval 1007 [SInt].

The used image and voice file number 1003 includes a target file number 1008 [Target_File_No] and a standard file number 1009 [Standard_File_No].

(Examination Data Creation Section Flow)

Next, a process flow of the examination data creation section 107 will be described with reference to FIG. 8. This process flow is executed by the cognitive function examination control section 109 upon receiving the result of the test flow, immediately after the test flow execution of FIG. 7, or when receiving a call from the watcher.

When this process flow is executed at the time of receiving a call from the watcher, the process flow may be executed immediately after the call from the watcher, or after the end of the call from the watcher.

Figure 8:
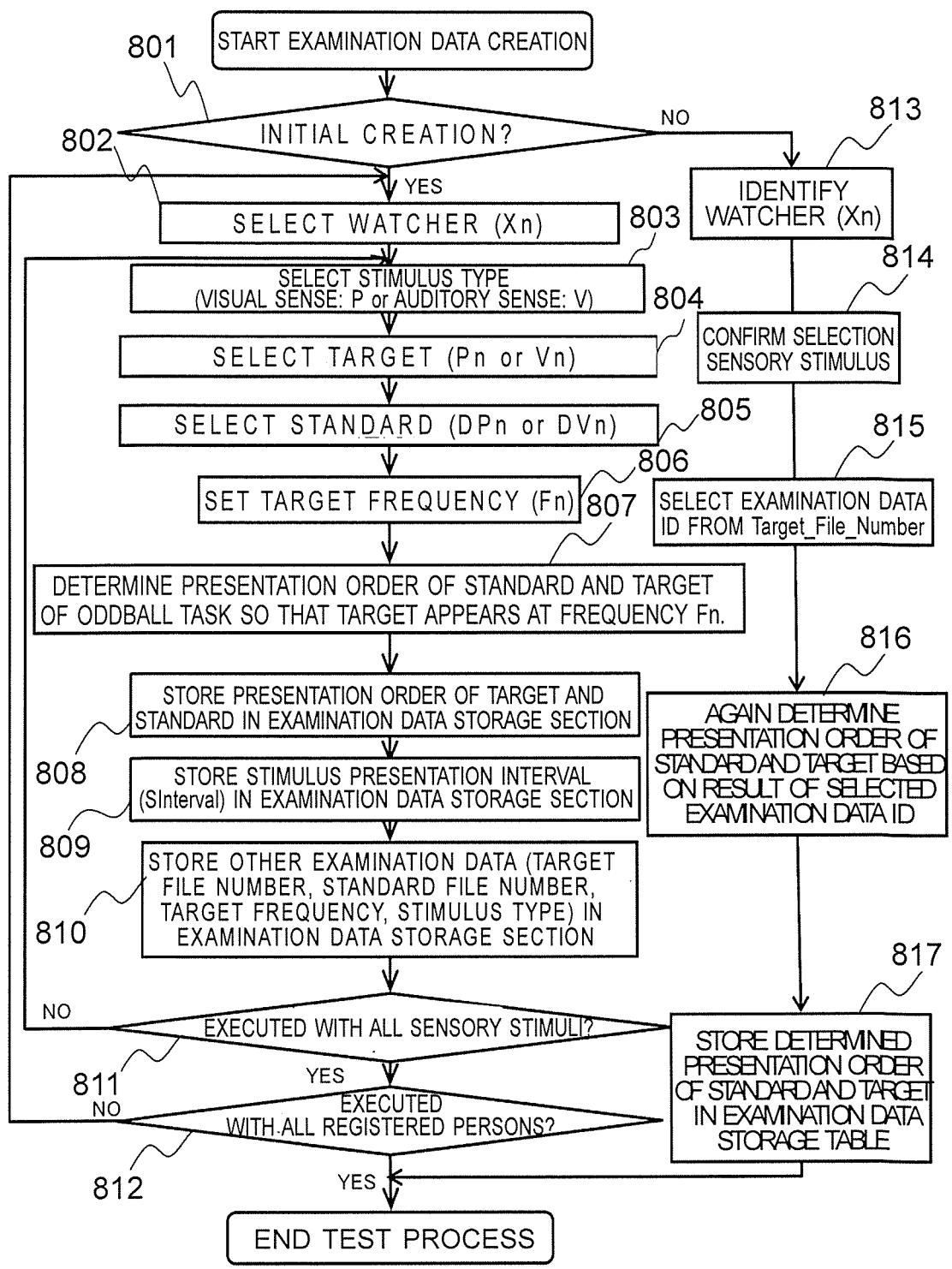
FIG. 8 is a flowchart of an examination data creation section.

A flow of FIG. 8 shows an example in which the process flow is implemented immediately after a call from the watcher.

The cognitive function examination control section 109 checks whether or not the examination data is stored in the examination data storage table, and confirms whether or not a first creation is to be performed (Step 801), and if the first creation is to be performed ("YES" in Step 801), the cognitive function examination control section 109 selects watcher Xn of the watcher table 501 (Step 802). The first examination data creation is performed immediately after execution of the test flow of FIG. 7.

Next, the examination data creation section 107 selects the type of test stimulus to be created (Step 803). The stimulus type is selected from the registered stimulus types with reference to the selection sensory stimulus 517 and the stimulus type 522 of the watcher table 501 and the standard table 520 of the oddball task data storage section 103. When image data that is visual data and voice data of auditory data are stored, the examination data creation section 107 selects "P" or "V".

Then, the examination data creation section 107 refers to the watcher table 501 which is located in the oddball task data storage section 103, and selects the image data file number 509 in the case of a picture which is a target or the voice data file number 513 in the case of a voice which is a target (Step 804).

When the visual sense is selected in Step 803, the examination data creation section 107 selects the picture data item 507 of the watcher, and when the auditory sense is selected, the examination data creation section 107 selects the voice data item 508 of the watcher. At this time, in the case of the [Validity] picture 510, the examination data creation section 107 selects 510 whose value is "1", and in the case of the voice, the examination data creation section 107 selects 514 whose value is "1".

Next, the examination data creation section 107 refers to the standard table 520 in the oddball task data storage section 103 and selects a standard image or voice (Step 805). When the examination data creation section 107 selects the visual data "P" in Step 803, the examination data creation section 107 selects the visual data in which the value of the stimulus type [Stimulus_Type] 522 of the standard table 520 is "P" and the value of the data validity [Validity] 523 is "1".

Next, the examination data creation section 107 refers to the watcher table 501 and sets the target frequency Fn (frequency 511 in the case of a picture and frequency 515 in the case of a voice) of the selected target (Step 806).

Next, the examination data creation section 107 determines the standard of the oddball task and the order of presentation of the targets so that the target appears at the frequency Fn set in Step 806 (Step 807).

Next, the examination data creation section 107 stores the target and standard presentation order determined in Step 807 in the stimulus order 1006 of the examination data storage table 1001 of the examination data storage section 108 (Step 808).

In the stimulus order 1006, for example, a symbol "T" indicating the target and a period symbol "S" indicating the standard may be used to store the order of those targets and the standard as a stimulus order.

Then, the examination data creation section 107 stores the selected target stimulus presentation interval (SInterval 512 in the case of the picture, SInterval 516 in the case of the voice) in the stimulus presentation interval [SInt] 1007 of the examination data storage table 1001 of the examination data storage section 108 (Step 809).

The examination data creation section 107 stores other examination data in the examination data storage table 1001 of the examination data storage section 108 (Step 810).

Specifically, the examination data creation section 107 stores the file number of the target selected in Step 804 in [Target_File_No] 1008 of the file number 1003 of the used image or voice in the examination data storage table 1001. Further, the examination data creation section 107 stores the standard file number selected in Step 805 in [Standard_File_No] 1009 of the file number 1003 of the used image or voice in the examination data storage table 1001.

The examination data creation section 107 stores the target frequency Fn set in Step 806 in the target frequency [Target_Frequency] 1004 of the examination data storage table 1001.

The examination data creation section 107 stores the stimulus type set in Step 803 in the stimulus type [Stimulus_Type] 1005 of the examination data storage table 1001. The examination data creation section 107 stores "P" in the case of the picture and "V" in the case of the voice.

The examination data creation section 107 refers to the selection sensory stimulus 517 of the watcher table 501, confirms whether or not execution has been made with all of the sensory stimuli registered (Step 811), and if the execution has been made with all of the sensory stimuli ("YES" in Step 811), the examination data creation section 107 confirms whether or not the execution has been made with all registrants registered in the watcher table (Step 812).

If the execution has been made with all the registrants ("YES" in Step 812), the process is terminated. If the execution has not been made with all the registrants ("NO" in Step 812), the examination data creation section 107 selects another watcher (Step 802).

Returning to Step 811, the examination data creation section 107 confirms whether or not the execution has been made with all senses. If the execution has not been made with all the senses ("NO" in Step 811), the examination data creation section 107 selects another stimulus type (Step 803).

Returning to Step 801, the examination data creation section 107 confirms whether or not the first creation is to be performed ("NO" in Step 801). If the first creation is not to be performed ("NO" in Step 801), the examination data creation section 107 identifies the watcher Xn (Step 813), refers to the selection sensory stimulus 517 in the watcher table 501, and confirms the selection sensory stimulus (Step 814).

Next, the examination data creation section 107 searches one of [File_NumberPicture_File_No] 509 and [Voice_File_No] 513 of the selective stimulus selected in Step 813, and checks ID with the examination data [ID No] 1002 with reference to [Target_File_No] 1008 of the used image or voice file number 1003 based on the searched result (Step 815). The examination data creation section 107 again determines the presentation order of the standard and the target based on the examination data of the examined examination data ID (mainly target frequency 1004) (Step 816).

The examination data creation section 107 stores and updates the result in Step 816 as a stimulus order 1006 of the examination data storage table 1001, and completes the processing (Step 817).

(Overall Cognitive Function Examination Process Flow)

Figure 9:
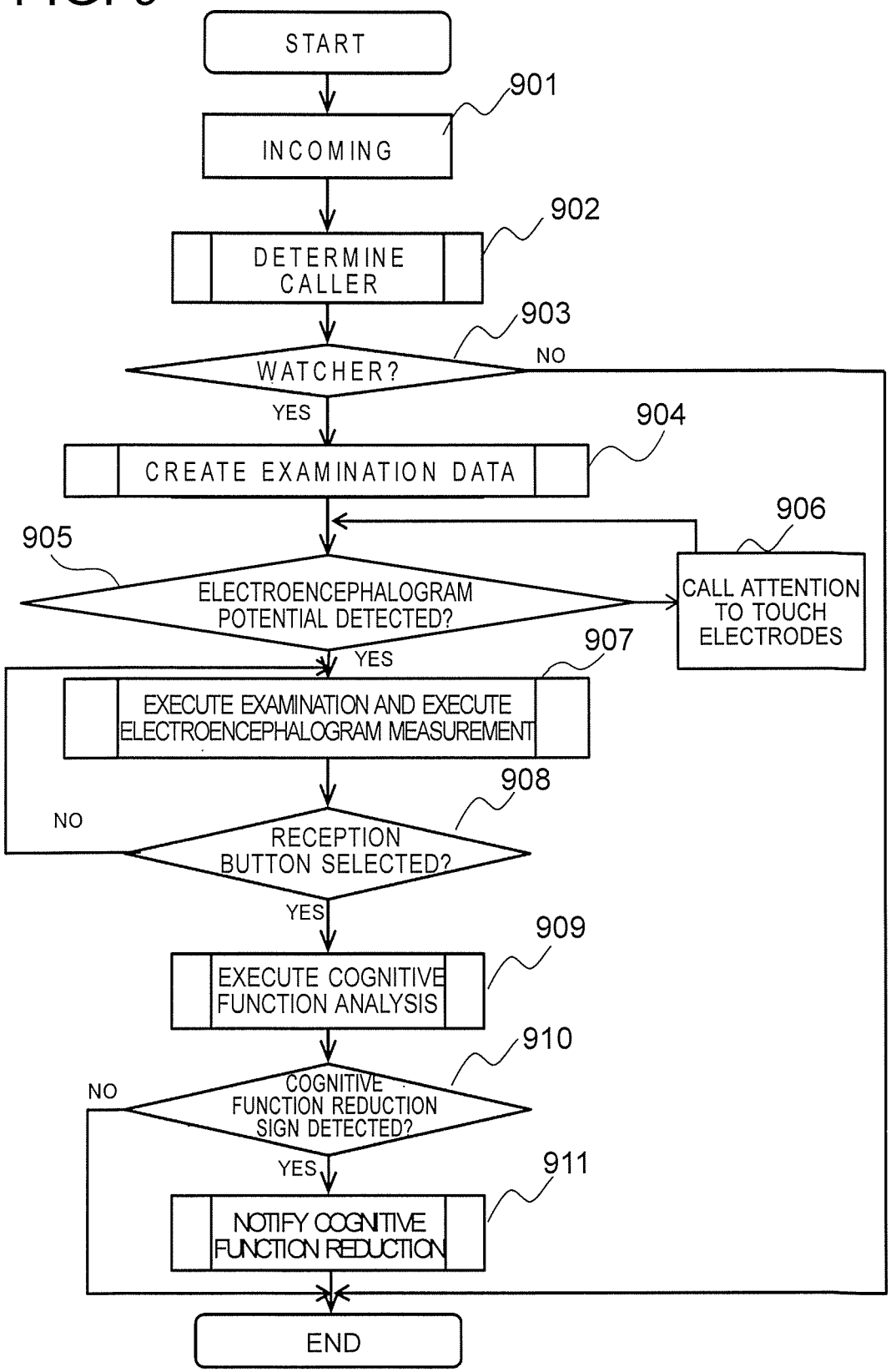
FIG. 9 is a flowchart of an overall process of a cognitive function examination of the smartphone into which a dementia examination function is implemented.

Next, a process flow of the overall cognitive function examination will be described with reference to FIG. 9. A flow in FIG. 9 is executed by the cognitive function examination control section 109 when the smartphone is activated.

In a relation with FIG. 6, FIG. 6A corresponds to Step 901, FIG. 6B corresponds to Step 905, and FIGS. 6C and 6D correspond to Step 907.

When someone calls a user's smartphone, the smartphone is in an incoming state. In response, this process flow receives an incoming call (Step 901), and executes a caller determination process using the incoming call as an event (Step 902).

Specifically, the cognitive function examination control section 109 checks whether or not the phone is registered in the table with reference to the watcher table 501, based on the telephone number at the time of incoming call, to thereby confirm whether or not the caller is a watcher (Step 903). If not ("NO" in Step 903), the process is terminated.

If the caller is a watcher ("YES" in Step 903), the cognitive function examination control section 109 executes the examination data creation processing described above, to generate examination data (Step 904).

Next, the cognitive function examination control section 109 checks whether or not an electroencephalogram potential has been detected (Step 905). If not detected ("NO" in Step 905), the cognitive function examination control section 109 urges the caller to touch the electrodes by display on the screen, voice, or the like (Step 906). In order to prevent reception from the use without confirming the caller, the cognitive function examination control section 109 may perform display or announcement for calling attention to confirm the caller when the caller is found to be a watcher or when an electroencephalogram potential is detected.

When the electroencephalogram potential has been detected in Step 905 ("YES" in Step 905), the cognitive function examination control section 109 executes the examination execution and the electroencephalogram measurement process (Step 907).

Specifically, the cognitive function examination control section 109 executes the examination with reference to the examination data storage table 1001 of the examination data storage section 108, and instructs the electroencephalogram measurement section 105 to start the electroencephalogram measurement.

Next, the cognitive function examination control section 109 confirms whether or not the reception button has been selected (Step 908). If the reception button has been selected ("YES" in Step 908), the cognitive function examination control section 109 terminates the examination and the electroencephalogram measurement process, and executes the cognitive function analysis (Step 909).

The cognitive function analysis in Step 909 is in charge of the cognitive function analysis section 111, the cognitive function examination control section 109 receives an event caused by depression of a reception button, and issues an instruction to the cognitive function analysis section 111 to execute the cognitive function analysis.

In the cognitive function analysis in Step 909, the cognitive function analysis section 111 calculates a value of P300 according to the electroencephalogram measurement result, and compares the calculated value with the analysis data set in advance, thereby detecting a sign of cognitive function reduction.

If the reception button has not been selected in Step 908 ("NO" in Step 908), the cognitive function examination control section 109 continues the examination test execution and the electroencephalogram measurement as they are (Step 907).

The cognitive function examination control section 109 confirms from the analysis result of Step 909 whether or not a sign of cognitive function reduction has been detected (Step 910), and if not detected ("NO" in Step 910), the processing is terminated. If the sign of cognitive function reduction has been detected ("YES" in Step 910), the cognitive function examination control section 109 executes a cognitive function reduction notification process (Step 911), and the process is terminated.

The cognitive function reduction notification in Step 911 is in charge of the cognitive function reduction notification section 113, and the cognitive function analysis section 111 issues an instruction to the cognitive function reduction notification section 113 upon receiving the sign of the cognitive function reduction whereby the cognitive function reduction notification is executed.

Further, in the cognitive function reduction notification in Step 911, the cognitive function examination control section 109 transmits the analysis result to the watcher registered in the watcher table with the use of the registered mail address. Alternatively, the cognitive function examination control section 109 displays the analysis result on the display section 115 and notifies the user himself or herself of the analysis result.

In a flow of FIG. 9, the cognitive function reduction notification section 113 performs the cognitive function reduction notification in response to the detection of the cognitive function reduction sign, but may notify the user of the analysis result regardless of the sign detection result.

In the present embodiment, a mail is used as how to contact the watcher but the present invention not limited to this method.

If a result close to the P300 value of the AD patient is obtained, the user may be prompted to go to a hospital directly or be automatically notified a specialized department such as a local government.

In this case, in this flow, the detection confirmation of the electroencephalogram potential in Step 905 may be executed before the examination data creation in Step 904 or before the caller determination in Step 902.

In addition, in the examination data creation in Step 904, examination data for use at the next incoming call at the time or after the previous incoming call may be generated in advance and stored in the examination data storage section 108, and the examination data may be read.

(Example of Test Data for Oddball Task)

Next, an execution example of the oddball task used in the execution of the examination and the electroencephalogram measurement in Step 907 in FIG. 9 will be described with reference to FIG. 11.

Figure 11A:
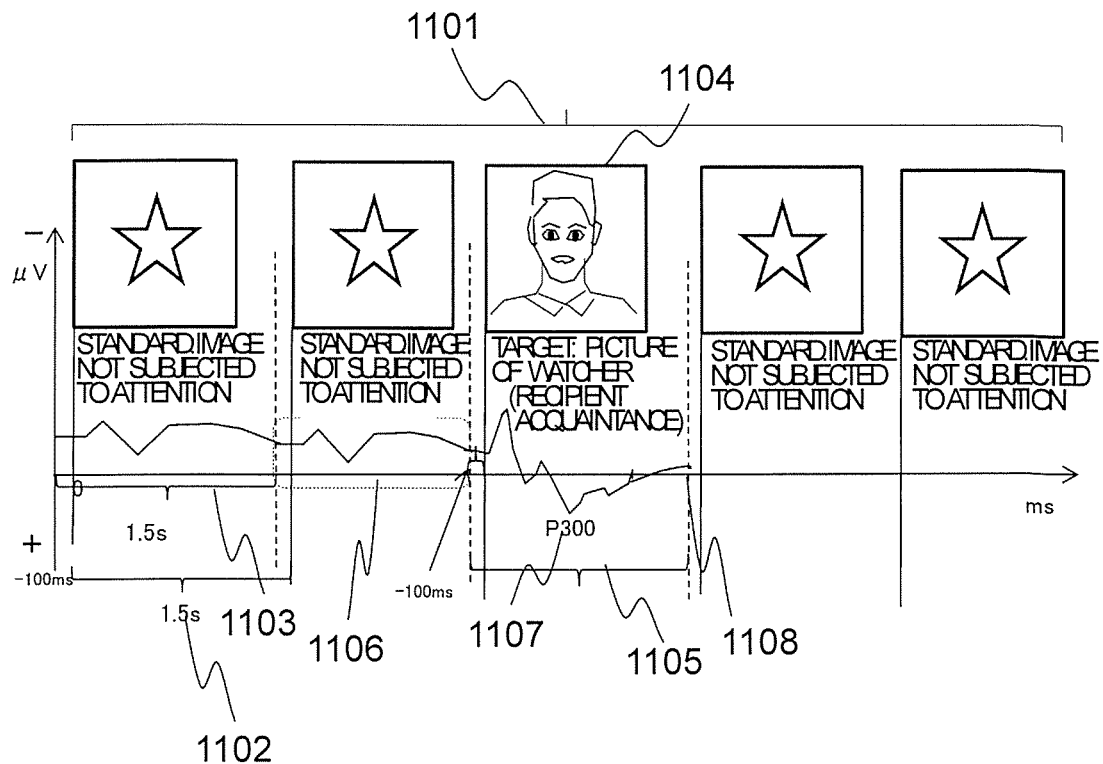
FIG. 11A is a diagram showing one example of test data for an oddball task (visual stimulus).

FIG. 11A shows an example of the oddball task in which the type of examination data is visual data, that is, an image visual stimulus. In this example, star marks of the standard image (FIG. 11A) and a person of the target image (FIG. 11A, 1104) are displayed as the examination data at predetermined time intervals.

In FIG. 11A, a horizontal axis represents a time (ms), and a vertical axis represents a potential (μV). An upper part of the graph shows a negative potential and a lower part of the graph shows a positive potential. An upper part 1101 of the graph shows a presentation timing of the examination data image.

The image presentation interval is 1.5 s (reference numeral 1102). This time is an estimated time, and the present invention is not limited to this time. The presentation interval is set based on a value described in the stimulus presentation interval 1007 of the examination data storage table 1001.

A measurement range of an electroencephalogram in the target and standard stimulus images is assumed to be a period of 1.5 s including 100 ms before those stimuli are presented (reference numeral 1103, which is an estimated time, and the present invention is not limited to this time).

Incidentally, in order to make it possible to verify the validity of the examination result later, the measurement of the electroencephalogram is performed not only on the target but also on the standard, and the measurement result is stored. Only the electroencephalogram for the target can be measured and stored in relation to a storable data capacity.

The images of the standards and the target are reproduced according to the stimulus order 1006 stored in the examination data storage table 1001 of the examination data storage section 108 shown in FIG. 10 and the stimulus presentation interval 1007 of the same table 1001. FIG. 11A shows an example in which the stimulus presentation interval 1007 is set to 1.5 s.

The lower part of the graph shows an example of an electroencephalogram that is measured when an image of examination data is presented. An example of FIG. 11A is an example in which a picture of the target watcher is presented thirdly and the reception button is depressed immediately after the third picture. In an example of FIG. 11A, since the electroencephalogram is measured until the reception button is selected, the electroencephalograms for the fourth and fifth standards are not measured.

In an example of FIG. 11A, when a third image of the target is presented, P300 appears at 1107 in the electroencephalogram 1104 (waveform in a period indicated by reference numeral 1105), but P300 does not appear in the electroencephalogram when first and second images of the standard are presented.

In an example of FIG. 11A, as a measurement result of the electroencephalogram at the time of target presentation, a waveform (waveform in a period indicated by reference numeral 1105) in a period of 1.5 s from 100 ms before the target stimulus is presented to 100 ms (point 1108) before a next standard stimulus is presented is assumed to be used in the cognitive function analysis section 111.

In the example of FIG. 11A, the electroencephalogram measurement is terminated when the user selects the reception button, but the measurement is continued at least until an end point 1108 of the electroencephalogram measurement period for the target. For that reason, even if the reception button is selected before the end point 1108, the measurement is continued until the end point 1108.

Figure 11B:
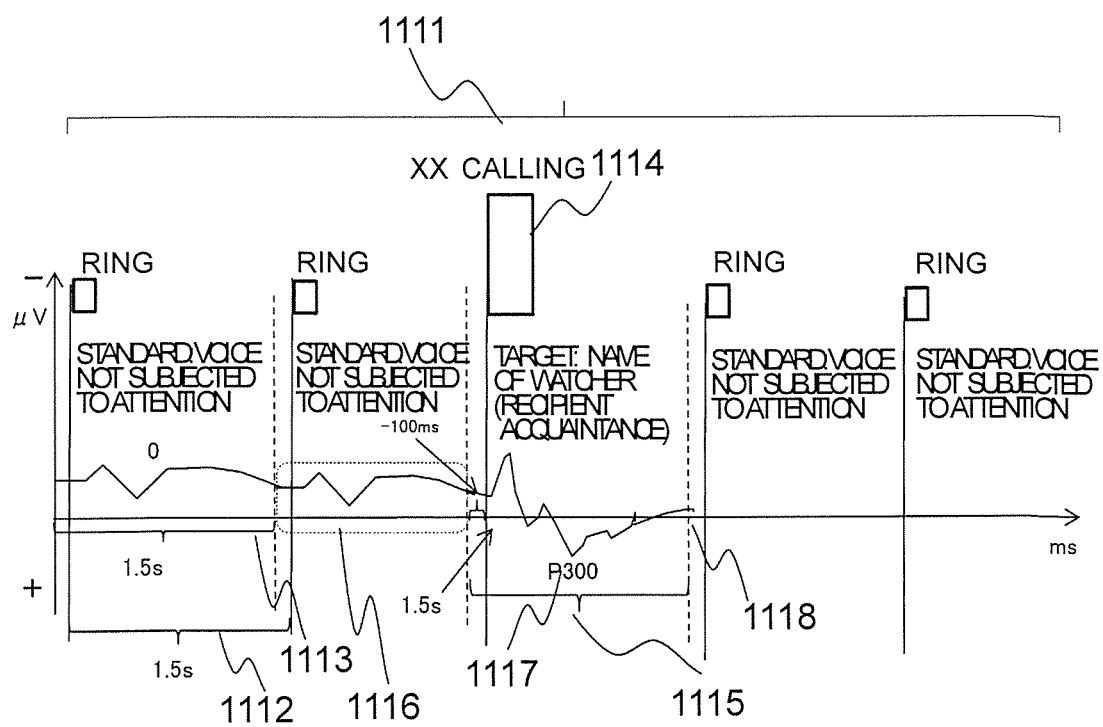
FIG. 11B is a diagram showing another example of the test data for the oddball task (auditory stimulus).

FIG. 11B shows an example of an oddball task in which the type of examination data is auditory data, that is, voice auditory stimulus.

In the present example, a call voice "ring, which is the voice (FIG. 11B) of the standard, and a voice by which a name of the watcher, which is the target voice (1114 in FIG. 11B) are output at predetermined time intervals.

Similar to FIG. 11A, a horizontal axis represents a time (ms), and a vertical axis represents a potential (μV). An upper part of the graph shows a negative potential and a lower part of the graph shows a positive potential. An image 1111 at the upper part of the graph shows a presentation timing of the examination data voice.

The stimulus presentation interval is set to 1.5 s (reference numeral 1112). This time is a standard time, and the present invention is not limited to this time.

The presentation interval is set based on the value described in the stimulus presentation interval 1007 of the examination data storage table 1001.

The measurement range of the electroencephalogram for the target and standard stimulus voices is 1.5 s including 100 ms before the stimulus is presented (reference numeral 1113). This time is an estimated time and the present invention is not limited to this time.

In order to make it possible to verify the validity of the examination result later, the measurement of the electroencephalogram is performed not only on the target but also on the standard, and the measurement result is stored. Only the electroencephalogram for the target due to the storable data capacity can be measured and stored.

The voices of the standard and the target are reproduced according to the stimulus order 1006 stored in the examination data storage table 1001 and the stimulus presentation interval 1007 of the same table 1001. In addition, FIG. 11B shows an example when the stimulus presentation interval 1007 is set to 1.5 s.

The reproduction is performed according to the stimulus order 1006 stored in the examination data storage table 1001 of the examination data storage section 108 in FIG. 10.

A lower part of the graph shows the electroencephalogram that is measured when the examination data is presented.

The example of FIG. 11B is an example in the case where the voice with which the name of the target watcher is read is presented thirdly and the reception button is pressed immediately after the presentation.

In the example of FIG. 11B, since the electroencephalogram is measured until the reception button is selected, the electroencephalograms for the standards presented in the fourth and fifth pictures are not measured. In the example of FIG. 11B, P300 appears in the electroencephalogram (a waveform in a period indicated by 1115) when the voice 1114 as a target is presented thirdly (reference numeral 1117), but P300 does not appear in the electroencephalogram when the voices as the standard are presented firstly and secondly.

A part used in the cognitive function analysis section 111 as an electroencephalogram at the time of target presentation is a waveform in a period of 1.5 s from 100 ms before the target stimulus 1114 is presented to 100 ms (point 1108) (waveform in a period indicated by reference numeral 1115) before the next standard stimulus is presented.

In the example of FIG. 11B, the measurement of the electroencephalogram is terminated when the user selects the reception button, but the measurement is continued at least until an end point 1118 of the electroencephalogram measurement period for the target. For that reason, even when the reception button is selected before the end point 1118, the measurement is continued until the end point 1118.

(Table Configuration Example of Electroencephalogram Data Storage Section)

Next, a configuration example of an electroencephalogram data table stored in the electroencephalogram data storage section 106 will be described with reference to FIG. 12.

An electroencephalogram data table 1201 includes an ID No. 1202, a caller (watcher) name 1203 [Name], a stimulus type 1204 [image [P] or voice [V]], a measurement time 1205 [a measurement start time 1206 and a measurement end time 1207], measurement data 1208 (μV, per 5 ms), target and standard file numbers 1209 [Target_File_No1210, Standard_File_No1211], a target frequency 1212 [Target_Frequency], a stimulus order 1213 [Or1, Or2, Or3, Or4, Or5, . . . , OrN], and a stimulus interval 1214 [SInt].

The measurement data 1208 is stored at an interval of 5 ms in real time by the cognitive function examination control section 109 upon receiving the result of measurement by the electroencephalogram measurement section 105 (an equivalent or more waveform may be measured, and the interval is not limited to the above value).

The target and standard file numbers 1209 [Target_File_No1210, Standard_File_No1211] store the target and standard file numbers used in the examination.

The target frequency 1212 stores the target frequency at the time of the examination.

The stimulus order 1213 stores the reproduction order of the target and standard files. For example, the stimulus order 1213 may be indicated by the order of symbols in the case where the target is "t" and the standard is "s".

The stimulus interval 1214 stores an interval at which the stimulus is presented at the time of examination.

(Table Configuration Example of Analysis Data Storage Section)

Next, a configuration example of the analysis data storage table stored in the analysis data storage section 110 will be described with reference to FIG. 13.

An analysis data storage table 1301 includes an ID No. 1302, a data type 1303, a measurement period 1304 of data during which the analysis data is calculated, a peak latency time average value 1305 (ms) of P300, a delay ratio 1306 [%] from a period average value during a past peak latency time, a peak latency time 1307 (ms) of P300 used in the determination of the presence or absence of the sign, and a required sample number 1308. In this example, the required sample number 1308 indicates the number of samples of electroencephalogram data required when the P300 of the target electroencephalogram is obtained by averaging.

In the example of FIG. 13, three types are set as the analysis data type [DataType] 1303.

One of the analysis data type 1303 is analysis data derived from the user's past examination results. The analysis data type is indicated by a value "1" of variable [DataType] (defined by SelfLog) (reference numeral 1309). The data measurement period 1304 for calculating the analysis data is a data measurement period for calculating the analysis data. The peak latency time average value 1305 of P300 stores the peak latency time average value of P300 during this measurement period. The sign of cognitive function reduction is calculated based on a value obtained by setting a certain delay ratio to the peak latency time average value 1305 of P300. This delay ratio is a delay ratio 1306 (%) from the period average value during the past peak latency time. Moreover, a value obtained by multiplying the delay ratio 1306 (%) from the average period value during the past peak latency time to the peak latency time average value 1305 of P300 is a peak latency time 1307 (ms) of P300 used in the determination of the presence or absence of the sign.

The remaining two analysis data types 1303 are set as general data.

One of the remaining two analysis data types 1303 is an average value of the user's ages. The average value is indicated by a value 2 (defined by AgeAve) of the variable [DataType](reference numeral 1310). This value is stored in the peak latency time 1307 of P300 used in the determination of the presence or absence of the sign. The data measurement period 1304 during which the analysis data is calculated, the peak latency time average value 1305 of P300, the delay ratio 1306 (%) from the period average value during the average peak latency time, and the required sample number 1308 are related to SelfLog 1309, all of those values are set to "0".

The other analysis data type 1303 is indicated by a value 3 (defined by ADAgeAve) of a variable [DataType] which is an age average value of AD patients (reference numeral 1311).

This value is stored in the peak latency time 1307 of P300 used in the determination of the presence or absence of the sign.

The data measurement period 1304 during which the analysis data is calculated, the peak latency time average value 1305 of P300, the delay ratio 1306 (%) from the period average value during the average peak latency time, and the required sample number 1308 are related to SelfLog 1309, all of those values are set to "0".

The data measurement period 1304 in which the analysis data is calculated includes a start date 1312 [Start: YYYY-MM-DD] and an end date 1313 [YYYY-MM-DD].

A data entry example of SelfLog 1309 of the data type 1303 is shown in 1314.

A data entry example of AgeAve1310 of the data type 1303 is shown in 1315.

A data entry example of ADAgeAve 1311 of the data type 1303 is shown in 1316.

In this example, in the average value of 1310 [AgeAve] for each age and the age average 1311 [ADAgeAve] of patients with Alzheimer's disease, data selected according to the user's age from the average value data that has been stored in the inside of the device from the beginning may be stored, or results obtained by accessing a medical database and searching according to the user's age may be stored when connectable to a network.

Incidentally, the data type 1303 to be compared is set in advance by initial setting or mode change.

(Table Configuration Example of Cognitive Function Analysis Result Storage Section)

Referring to FIG. 14, a configuration example of a table which is stored in the analysis result storage section 112 will be described.

A table 1401 of the cognitive function analysis result storage section includes an analysis result ID No. 1402, a calculation period 1403 of the data for calculating the average time of the peak latency time of P300, a caller 1404, a stimulus type 1405, an average peak latency time 1406 of P300, an analysis data type 1407 used in detecting the sign, and a sign presence or absence determination result 1408.

The data calculation period 1403 for calculating the average time at the time of the peak latency time of P300 includes a start date 1409 and an end date 1410.

In addition, the stimulus type 1405 is a visual stimulus [P]1411 or an auditory stimulus [V] 1412.

The average peak latency time 1406 of P300 is an average within the data calculation period, and its unit is ms.

In the [DataType] of the analysis data type 1407, when the user's past P300 peak latency time is used, a (SelfLog 1413) value "1" is stored, and when the average value of P300 peak latency time of the user age is used, an (AgeAve 1414) value "2" is stored, and when the average value of the P300 peak latency time of the age average of Alzheimer's disease patients is used, an (ADAgeAve 1415) value "3" is stored.

In the [Result] 1416 of the sign presence or absence determination result 1408, value "1" (reference numeral 1417) is set if there is a sign, and value "0" (reference numeral 1418) is set if there is no sign.

(Process Flow of Cognitive Function Analysis Section)

Figure 15:
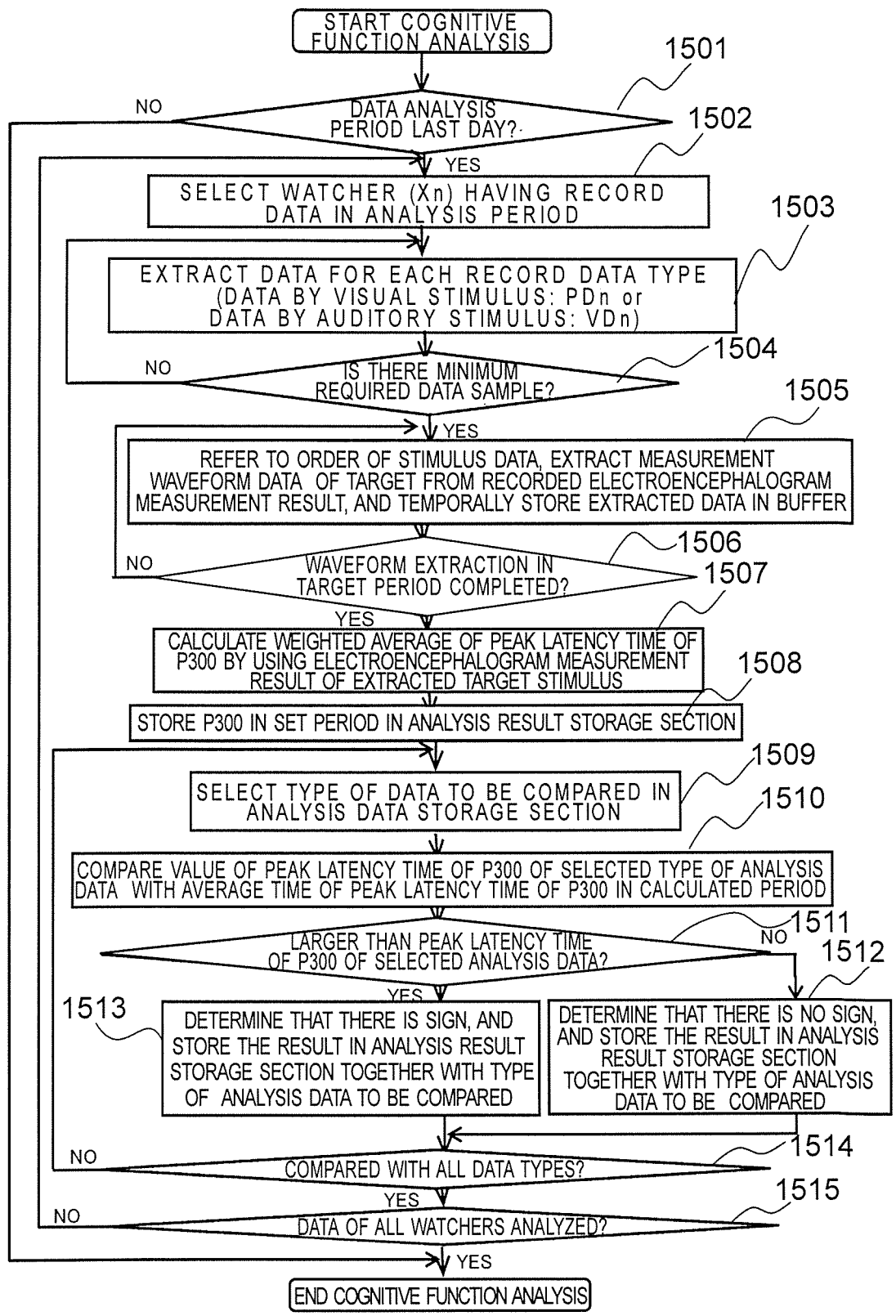
FIG. 15 is a flowchart of a cognitive function analysis section.

Next, processing contents of the cognitive function analysis section 111 according to the present invention will be described with reference to FIG. 15.

In the present embodiment, a description will be made on the assumption that the data analysis period is predetermined in advance. For example, the data analysis period may be the last day at an end of a month or the last day in a period determined by the user.

The cognitive function analysis section 111 performs a schedule management using a timer 119 in order to perform cognitive function data analysis on the electroencephalogram data. For example, the cognitive function analysis section 111 checks whether or not to reach the data analysis period to be executed next (Step 1501), and if not reached ("NO" in Step 1501), the process is terminated.

If the data analysis period has been reached ("YES" in Step 1501), the cognitive function analysis section 111 selects the watcher Xn with the stored data in the analysis period (Step 1502).

Next, the cognitive function analysis section 111 extracts data for each stored data type from the stored data within the analysis period (Step 1503). Specifically, the cognitive function analysis section 111 searches the watcher selected from the name 1203 of the caller (watcher) of the electroencephalogram data table 1201 and extracts the data for each stimulus type 1204 from the appropriate search result (Step 1503).

Next, the cognitive function analysis section 111 determines whether or not the data extracted in Step 1503 includes a minimum necessary data sample (Step 1504).

The minimum necessary data sample is examined by selecting SelfLog 1309 in the analysis data storage table 1301 and referring to the value of the required sample number 1308.

If there is a sample ("YES" in Step 1504), the cognitive function analysis section 111 refers to the order of the stimulus data, extracts the measured waveform data that appears for the target stimulus from the stored electroencephalogram data, and temporarily stores the extracted measured waveform data in the buffer (Step 1505).

The cognitive function analysis section 111 refers to the stimulus order 1213 of the electroencephalogram data table 1201 as the order of the stimulus data to check the order of "t", and calculates the time when the "t" appears according to the time of the stimulus interval. Then, the cognitive function analysis section 111 extracts the data of the time zone from the measurement data 1208. For example, if "t" is the third order and the stimulus interval is 1.5 s, the target is presented after approximately 3 s, and therefore, 3 to 4.5 seconds of the measurement data become appropriate data. In fact, data to be analyzed is 0.1 ms before the stimulus presentation, but since the measurement data is also measured from 0.1 second before the stimulus presentation, 3 seconds to 4.5 seconds of the measurement data may be extracted.

The buffer is provided on the RAM 213 and is managed by the cognitive function analysis section 111.

Next, the cognitive function analysis section 111 checks whether or not the waveform extraction for the target period has been completed from the results extracted in Step 1503 (Step 1506). If not completed ("NO" in Step 1506), the cognitive function analysis section 111 extracts the measured waveform data of the target, and temporarily stores the extracted result in a buffer (Step 1505). The buffer stores and saves a waveform identification number [Wave_No], a caller watcher [Name], a stimulus type [P] or [V], a measurement time (measurement start time: [Start_Time], measurement end time: [Start_Time]), a target waveform data μV, per 5 ms, and a stimulus interval [SInt].

In Step 1506, if the extraction of the waveform for the target period has been completed from the results extracted in Step 1503 ("YES" in Step 1506), the cognitive function analysis section 111 calculates the average of the P300 peak latency time with the use of the electroencephalogram data of the target stimulus accumulated in the extracted buffer (Step 1507).

Then, the cognitive function analysis section 111 stores the result of averaging P300 in a set period in the average peak latency time 1406 of P300 in the analysis result storage section 112 (Step 1508).

Next, the cognitive function analysis section 111 selects the data type 1303 to be compared from the analysis data storage table 1301 of the analysis data storage section 110 (Step 1509).

Then, the cognitive function analysis section 111 compares a value of the peak latency time 1307 of P300 used in the determination of the presence or absence of the sign of the selected data type 1303 with the average time for the peak latency time of P300 in the analysis period (Step 1510).

In Step 1510, if the average time is equal to or less than the value of the peak latency time 1307 of P300 used in the determination of the presence or absence of the sign of the selected data type 1303 ("NO" in Step 1511), the cognitive function analysis section 111 determines that there is no sign, and stores the determination result together with the type of analysis data to be compared in the table 1401 of the analysis result storage section 112 (Step 1512).

In Step 1510, if the average time is more than the value of the peak latency time 1307 of P300 used in the determination of the presence or absence of the sign of the selected data type 1303 ("YES" in Step 1511), the cognitive function analysis section 111 determines that there is a sign, and stores the determination result together with the type of analysis data to be compared in the average peak latency time 1406 of P300 in the table 1401 of the analysis result storage section 112 (Step 1513).

The cognitive function analysis section 111 checks whether to compare with all of the data types 1303 in the analysis data storage table 1301 (Step 1514), and if not compared ("NO" in Step 1514), the cognitive function analysis section 111 selects the type of data to be compared in the analysis data storage section 110 (Step 1509).

In the example of FIG. 13, three data types are registered. In that case, in Step 1514, the cognitive function analysis section 11 checks whether or not those three data types are compared.

The cognitive function analysis section 111 check if all the data types 1303 have been compared, and if compared ("YES" in Step 1514), the cognitive function analysis section 111 checks if all watchers' data has been analyzed (Step 1515), and if analyzed ("YES" in Step 1515), the process is terminated.

The cognitive function analysis section 111 checks whether to analyze the data of all the watchers with reference to the name 1203 of the caller (watcher) of the electroencephalogram data table 1201 (Step 1515), and if not analyzed ("NO" in Step 1515), the cognitive function analysis section 111 selects the watcher Xn with the stored data in the analysis period (Step 1502).

The reason for analyzing the electroencephalogram measurement data for each watcher is that the picture or voice presented to the user as a data stimulus used at the time of measurement differs for each watcher. The reason for analyzing the electroencephalogram measurement data for each stimulus vision or auditory sense is that a tendency of the peak latency time of P300 differs depending on the type of stimulus used.

(Example of Cognitive Function Analysis Result)

Figure 16:
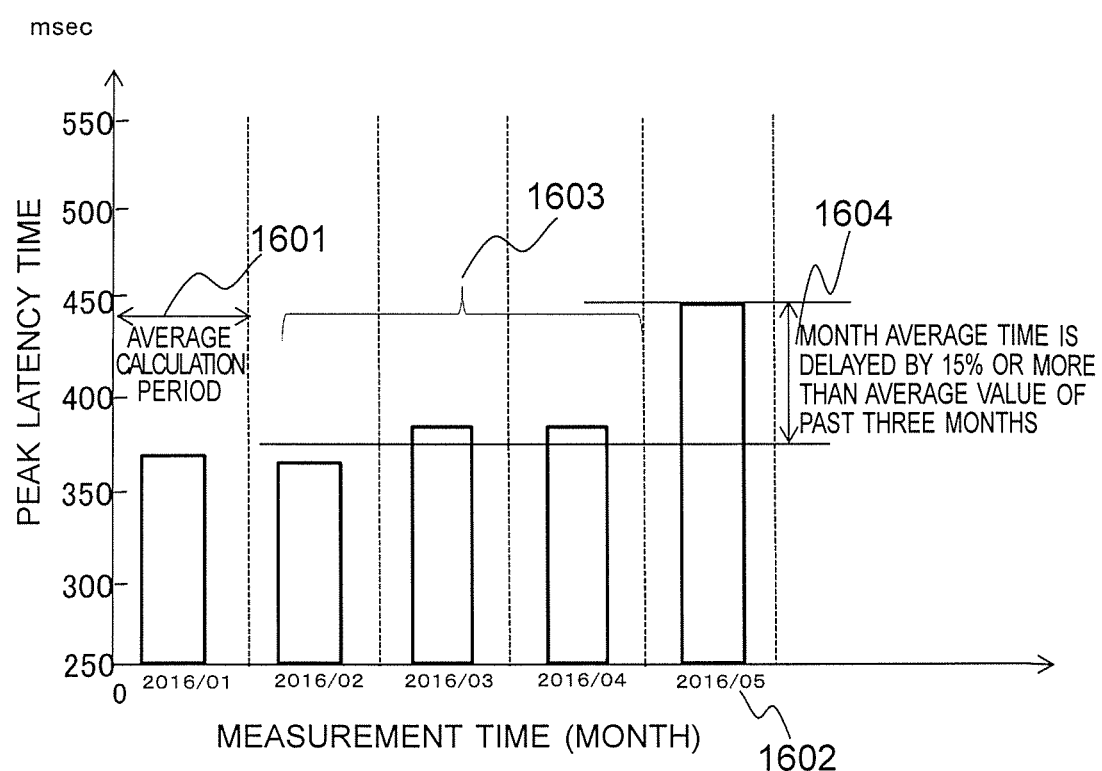
FIG. 16 is a diagram showing an example of a cognitive function analysis result.

FIG. 16 shows an example of the cognitive function analysis result for a specific watcher. In the example of FIG. 16, the average calculation period of the peak latency time is set to one month (reference numeral 1601) and the peak latency time of P300 every month is analyzed. A horizontal axis indicates a monthly unit during measurement, and a vertical axis indicates a peak latency time of P300.

In the example of FIG. 16, a case in which the average time at the peak latency time of P300 on the monthly basis is slowed by 15% or more in comparison with the results of the last three months is regarded as a sign of the reduction in the cognitive function and set in advance in the analysis data storage section 110.

Since May 2016 (reference numeral 1602) is slower than the average peak latency time 1603 of P300 for the past 3 months by 15% or more (reference numeral 1604), it is determined that there is a sign.

Incidentally, the result of FIG. 16 is calculated for each watcher. For that reason, there are cases in which a sign is determined to be present and in which a sign is determined to be absent depending on the watcher even in the same period. However, if any one person determines that there is a sign, it may be determined that there is a sign, or when the results for all registered watchers indicate that there is a sign, it may be finally determined that the sign is present.

The analysis result of the peak latency time of P300 as shown in FIG. 16 may be notified a specific watcher of when a sign is detected or whenever the result is calculated by monthly analysis.

According to the present embodiment, an oddball task is automatically generated, the task is automatically executed, and a function for automatically measuring an electroencephalogram during execution of the task is installed, thereby being capable of examining the state of cognitive function of the user (subject) in daily life. At that time, the user is less likely to be aware that the cognitive function examination is being performed because an oddball task is presented during an operation of a different purpose from the cognitive function examination, for example, during an answering operation of the telephone to acquire the electroencephalogram data for the task. As a result, a psychological burden feeling at the time when the user receives a cognitive function examination can be reduced.

Further, with the provision of the function for automatically analyzing the examination result, the state of the user's cognitive function can be periodically, checked.

Further, according to the present embodiment, the cognitive function examination data can be automatically generated with the use of a DB for storing an oddball task stimulus. In addition, the electroencephalogram measurement section detects that the electroencephalogram can be measured, and the cognitive function examination data automatically generated is executed upon the detection, and the electroencephalogram at that time can be measured and stored. In addition, the cognitive function examination can be implemented with the use of the user's priority sensory stimulus. As a result, the elderly can easily and continuously carry out the cognitive function examinations in daily life. Also, if the cognitive function reduction has been detected, the examination result can be notified the user or the watcher of the user concerned registered in advance of.

Second Embodiment

In the smartphone equipped with the function of the cognitive function examination described in the first embodiment, a typical phone usage behavior of paying attention to who is the caller is at the time of incoming call, and answering the call after confirming that the caller is an acquaintance according to an incoming image or an incoming voice is leveraged as an oddball task, and when a call arrives from a watcher, the incoming image or incoming voice generated automatically based on the oddball task is displayed or reproduced for the user, and the electroencephalogram P300 of the user induced in response to the displayed image or the reproduced voice is measured and analyzed to examine the cognitive function of the user.

As mentioned above, there are auditory, visual and somatic senses in stimulus inducing P300 in the oddball task. In general, there is a sense (predominance sense) that humans use preferentially among those senses, and the sense differs from one person to another. For that reason, the convenience of the user can be improved by using voice for persons who have an auditory advantage and images for persons who have a visual advantage for the oddball tasks, which can expect that the cognitive function examinations are implemented more frequently.

It is said that the superiority of the three senses can be understood by analyzing the predicates (verbs, adjectives, adverbs) of a language that is usually used. In the present invention, those senses are utilized to analyze the difference in the priority sense of each individual and to select the type of stimulus used in the cognitive function examination, such as visual or auditory. More specifically, the predicates are extracted from at least one of contents of a subject's speech and outgoing mails forwarded by the subject in the past, and a visual sensory predicate usage frequency and an auditory sensory predicate usage frequency indicated in the predicates are calculated. If the visual sensory predicate usage frequency is large, the visual stimulus is determined to be used as the type of stimulus of the examination data to be presented to the subject, and if the auditory sensory predicate usage frequency is large, the auditory stimulus is determined to be used as the type of stimulus of the examination data to be presented to the subject.

In order to analyze the predicates, the predicates are analyzed using a text database for language research called "corpus" available on the Internet, and the superiority of the sense of the user is analyzed.

In the present embodiment, in a device that can use, for example, visual and auditory data in which data of an email or call is analyzed by paying attention to the predicate to determine the sensory advantage of the user, and the type of the sensory data used in the examination is determined according to the determination result, there is equipped with a mechanism for determining whether to use a visual image or an auditory voice.

(Example of Cognitive Function Analysis Result)

Figure 17:
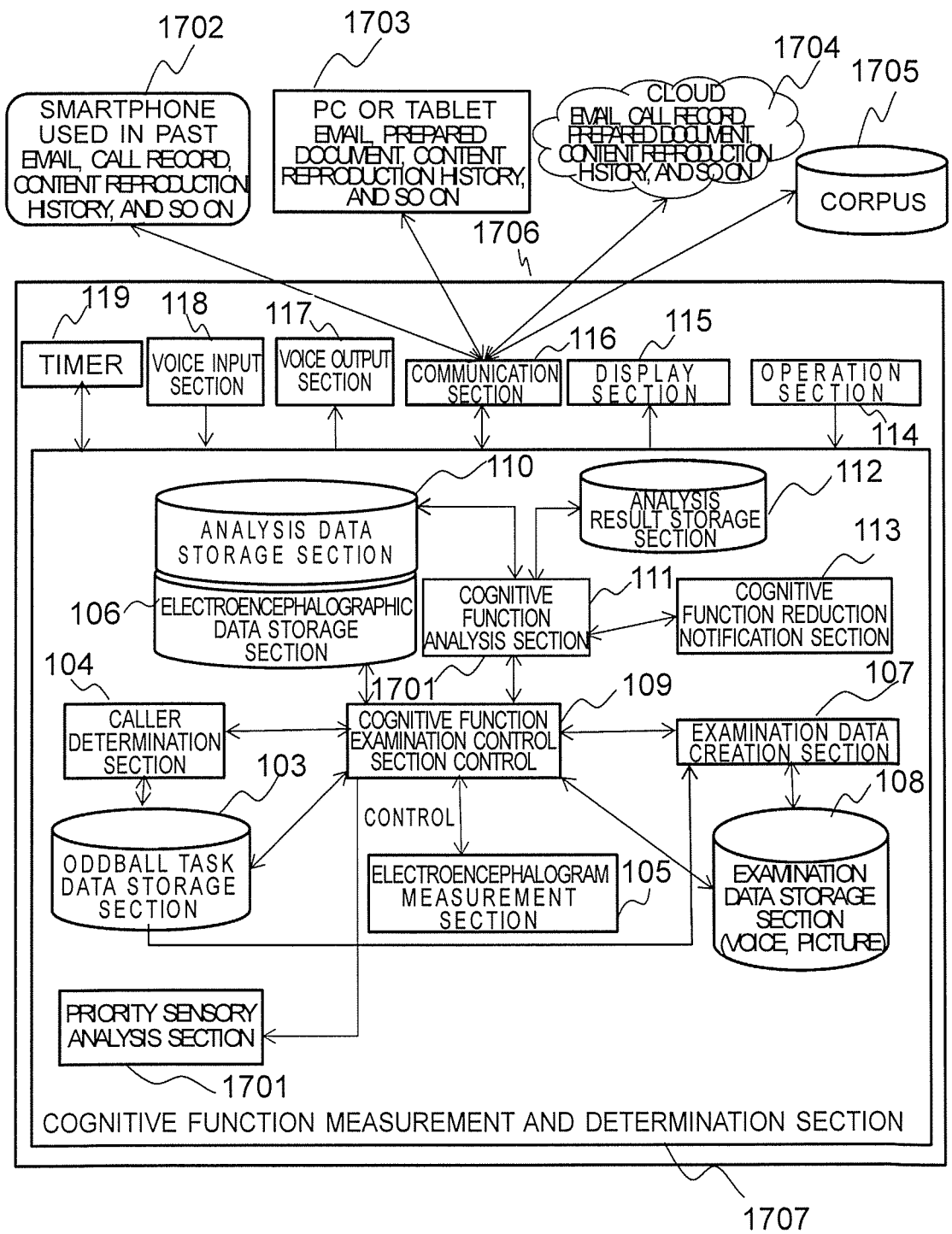
FIG. 17 is a functional block diagram of a cognitive function examination device having a priority sensory analysis section.

FIG. 17 is a functional block diagram of a cognitive function examination device (smartphone) used in the present embodiment.

A difference from FIG. 1 of the first embodiment resides in that a priority sensory analysis section 1701 is provided inside, which acquires user data (outgoing mail and call record) related to mails and calls stored in a memory in an information device (smartphone 1702, PC, or tablet 1703) connected to an external over the network through the communication section 116 or on a cloud 1704, and analyzes the priority sense of the user.

Cases in which individuals have multiple devices such as smartphones, PCs, and tablets are increasing. Along with those cases, in order to change terminal models and share various data between terminals, cases of uploading information such as emails, address books, images and voices using cloud services are increasing. In addition, there are cases in which the user's behavior history so far remains, such as a call record and a content reproduction history of a smartphone that is no longer used due to model change. In the present embodiment, in order to determine the priority sense of the user, those pieces of information are used.

Incidentally, when the priority sense is analyzed by the predicate (verb, adverb, adjective), the corpus 1705 described above is used.

The processing of the priority sensory analysis section 1701 is executed at the time of initial setting.

The cognitive function examination device 1706 according to the present embodiment includes the priority sensory analysis section 1701 that analyzes the priority sense of the user according to the user data (outgoing mail and call record) related to the mail or the call in the information device (1702, 1703) connected to the external through the communication section 116 or on the cloud 1704. The other functional blocks have the same block configurations as those in FIG. 1.

Incidentally, in the example of FIG. 17, the corpus 1705 provided on the Internet is used, but since a general-purpose corpus on the Internet takes time to search for vocabulary, a visual and auditory vocabulary analysis corpus may be created by using the corpus on the Internet, and the created corpus may be provided in the device.

Registration of data in the oddball task data storage section 103 may be performed by extracting data (phone numbers, names, mail addresses, voices, pictures of the watcher) to be registered in the oddball task data storage section 103 from data of the address book already recorded in the smartphone, or pictures recorded in an album or data recorded in a call record by the user, or may be performed by using data newly transmitted from the watcher.

Moreover, data may be registered in the oddball task data storage section 103 by using data stored in another smartphone or on a cloud connectable to the network.

(Priority Sensory analysis Process Flow)

Next, the contents of the priority sensory analysis process executed by the priority sensory analysis section 1701 which is a feature of the present invention will be described with reference to FIG. 18.

At the initial setting of the present embodiment, the priority sensory analysis section 1701 attempts to connect to an external device (1702, 1703) or the cloud 1704 through the communication section 116 (Step 1801). The priority sensory analysis section 1701 checks whether or not to be connected to the external device or the cloud (Step 1802). If not connectable ("NO" in Step 1802), the priority sensory analysis section 1701 checks if the connection fails N times or more (Step 1803). If the connection does not fall N times or more ("NO" in Step 1803), the priority sensory analysis section 1701 attempts to connect to the external device or the cloud (Step 1801). If the connection fails N times or more ("YES" in Step 1803), the process is terminated.

The priority sensory analysis section 1701 confirms whether or not to be connectable (Step 1802), confirms whether or not the user's past outgoing mail exists on the connected external device or cloud ("YES" in Step 1802) (Step 1804). If the outgoing mail exists ("YES" in Step 1804), the priority sensory analysis section 1701 performs a part-of-speech analysis on the outgoing mail (Step 1805). Then, the priority sensory analysis section 1701 extracts the predicates (verb, adjective, and adverb) from the result of the part-of-speech analysis (Step 1806).

Next, the priority sensory analysis section 1701 refers to the corpus 1705 on the Internet, extracts, from the extracted predicates, the vocabularies that suggest that the user used visual and auditory senses, classifies the vocabularies into visual sensory predicate or auditory sensory predicate, and analyzes the appearance frequency of visual sensory predicate and the appearance frequency of auditory sensory predicate appearing in the extracted predicates (Step 1807).

In this example, visual sensory predicates include vocabularies such as seeing, projecting, bright, shining, and dazzling. Auditory sensory predicates include vocabularies such as listening, saying, reverberating, noisy and quiet. The corpus that can be used on the Internet may be used as it is, or dedicated databases for vocabularies related to visual sensory predicates and auditory sensory predicates may be created using the data of the corpus on the Internet, and those databases may be provided in the device 1706.

Next, the priority sensory analysis section 1701 receives the result of the analysis of the appearance frequency of the visual and auditory sensory predicates in Step 1807, and checks whether or not the appearance frequency of the visual sensory predicates is high (Step 1808). If high ("YES" in Step 1808), the priority sensory analysis section 1701 sets the cognitive function examination control section 109 to the examination by the image, and the process is terminated (Step 1809). On the other hand, if the appearance frequency of the visual sensory predicates is not high ("NO" in Step 1808), the priority sensory analysis section 1701 sets the cognitive function examination control section 109 to the examination by voice (Step 1810), and the process is terminated.

In Step 1804, if there is no past outgoing mail of the user ("NO" in Step 1804), the priority sensory analysis section 1701 checks whether or not there is a past call voice record (Step 1811). If there is the past call voice record ("YES" in Step 1811), the priority sensory analysis section 1701 performs the part-of-speech analysis (Step 1805), and analyzes the priority sense. Before making a call analysis, there is a need to convert the part-of-speech into a text. In the conversion into the text data, text conversion software of the voice on the smartphone 1702, a PC or the tablet 1703, and the cloud 1704 in which the voice data has been recorded may be used. Alternatively, the text conversion software may be installed in the device of the present invention for conversion.

In Step 1811, if there is no past call voice record of the user ("NO" in Step 1811), the priority sensory analysis section 1701 checks whether or not there is a prepared sentence (Step 1812). If there is a prepared sentence ("YES" in Step 1812), the priority sensory analysis section 1701 performs the part-of-speech analysis on the sentence (Step 1805), and analyzes the priority sense. If there is no prepared sentence in Step 1812 ("NO" in Step 1812), the process is terminated. In that case, the priority sensory analysis section 1701 may implement the examination of the cognitive function by a default stimulus predetermined at the time of device shipment. The default stimulus may be a visual sensory stimulus or an auditory sensory stimulus.

Figure 18:
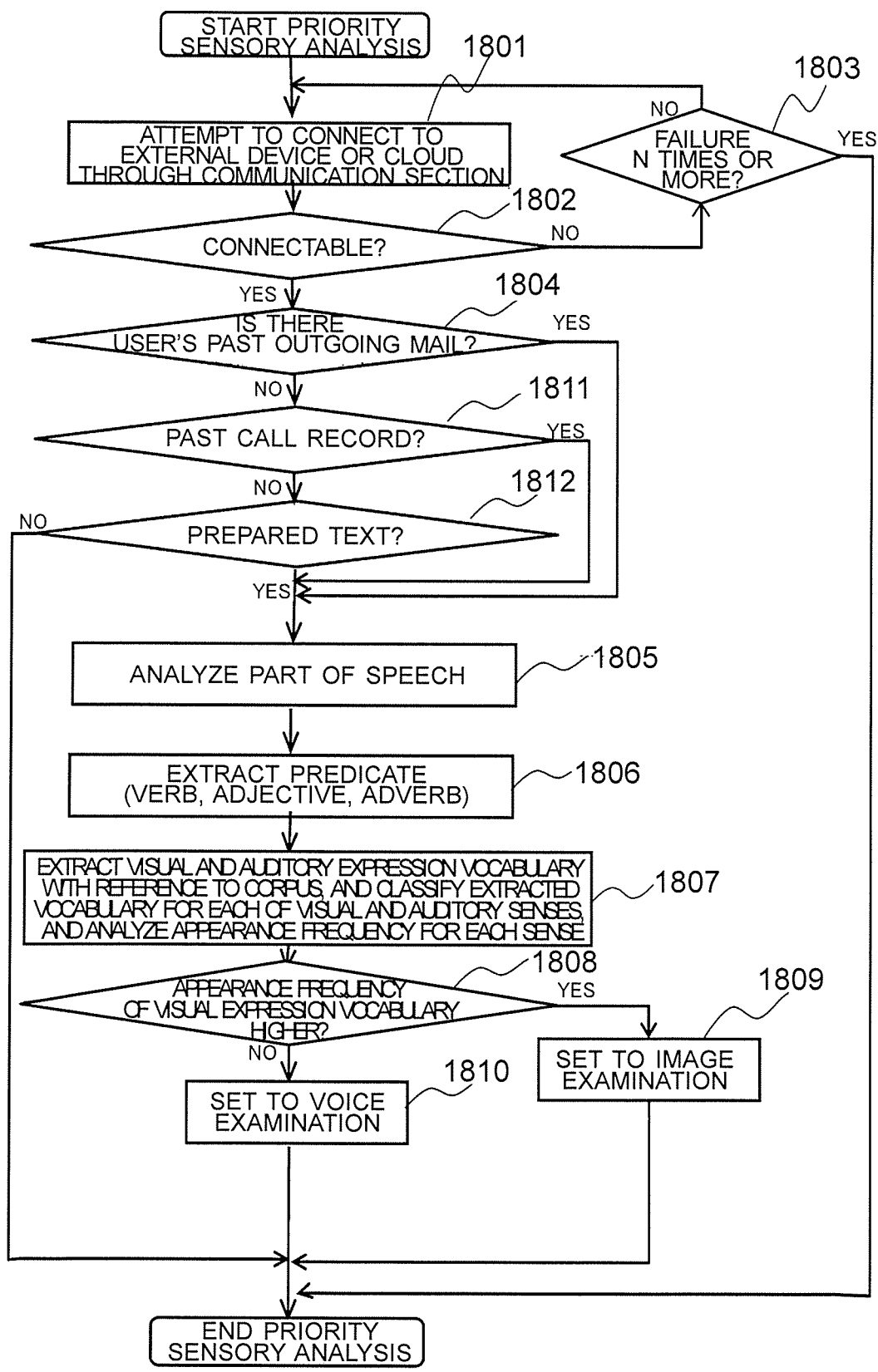
FIG. 18 is a flowchart of the priority sensory analysis section.

In this example, in FIG. 18, the priority sense is analyzed by analyzing the predicate, but the priority sense may be analyzed according to the content reproduction frequency. In other words, the reproduction frequencies of the image content and the voice content are checked, and if the reproduction frequency of the image content is higher, the examination by the image is set and the process is terminated. If the voice content reproduction frequency is higher, the examination by voice is set.

Also, the priority sensory analysis section 1701 may present a questionnaire for analyzing the priority sense, and analyze an answer of the question to determine the priority sense, so as to select the type of stimulus data used in the cognitive function examination based on the determination result.

As described above, the type of stimulus data used in the cognitive function examination is set based on the priority sense, but the type of stimulus data (image or voice) used in the cognitive function examination can be automatically changed according to the surrounding situation. For example, in a situation where the surroundings are disturbed by making a sound, the visual (image) data is used. Ambient conditions may be manually set by the user, or may be set from location information using information from a GPS or the like.

From the above description, the cognitive function examination device 1706 according to the present embodiment is equipped with the priority sensory analysis section 1701, thereby being capable of implementing the examination of the cognitive function with the use of the data of the sense preferentially used by the user.

Third Embodiment

A smartphone equipped with the function of the cognitive function examination described in the first and second embodiments implements the cognitive function examination by leveraging a scene, a timing, or both a scene and a timing where everyone acts on a daily basis, such as an incoming phone call from the watcher. As a result, early detection of dementia can be easily performed in daily operation without imposing a mental burden on the user, particularly the elderly, who undergoes a cognitive function examination.

In the present embodiment, an example in which a cognitive function examination is performed in daily operation other than an incoming call will be described. In addition, the smartphone used by the present embodiment is assumed to be provided with the configurations described in FIG. 1 and FIG. 17.

(Example pf How to Use Alarm)

FIG. 19 shows an image of how to use a cognitive function examination using the operation of an alarm (including an alarm clock and a schedule). The alarm function is executed by the timer 119. The user sets an alarm using an application (for example, an alarm application, a scheduler, and so on) that uses the timer 119.

Figure 19A:
FIG. 19A is a diagram shows an example of how to use alarm of the smartphone (at the time of ringing or vibration).

Upon arrival at a time (or event) set in advance by the user, the timer 119 causes an alarm sound to be reproduced or vibrated through the voice output section 117 and notifies the cognitive function examination control section 109 of this fact (FIG. 19A).

Figure 19B:
FIG. 19B is a diagram showing an example of how to use the alarm of the smartphone (held state).

When the user grasps the smartphone and a surface of his hand touches the electroencephalogram measurement electrodes 302 and 303 on the back of the smartphone or the electroencephalogram measurement electrodes 306 and 307 on the side, the cognitive function examination control section 109 detects that the electroencephalogram can be measured by the aid of the electroencephalogram measurement section 105 through the electrodes. In addition, the cognitive function examination control section 109 creates examination data with the aid of the examination data creation section 107, and displays the examination data on the display section 115 to start the cognitive function examination (FIG. 19B).

Figure 19C:
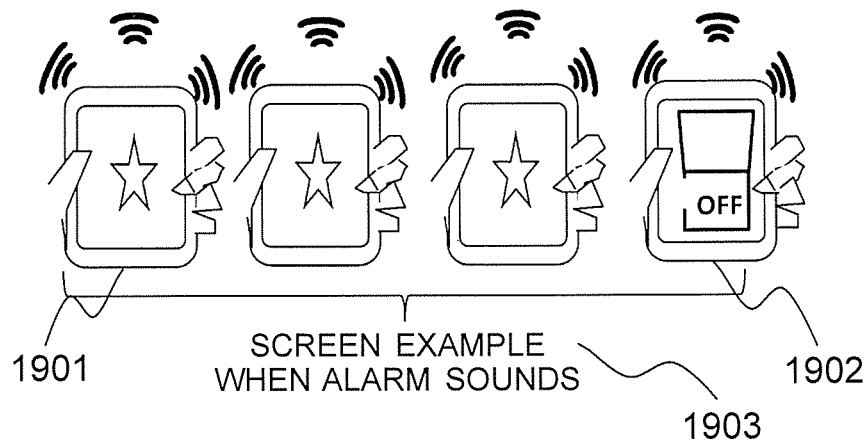
FIG. 19C is a diagram showing an example of how to use the alarm of the smartphone (visual stimulus).
Figure 19D:
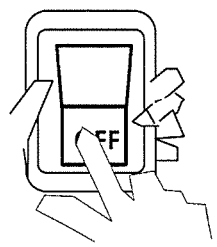
FIG. 19D is a diagram showing an example of how to use the alarm of the smartphone (OFF button display).

In order to turn off the alarm sound, the user views a screen on which the examination data created by the examination data creation section 107 is displayed on the display section 115 (FIG. 19C). On the screen, an image 1901 such as a pictograph as a standard stimulus for the oddball task and an icon 1902 of a switch OFF as a target are displayed on the screen at random. The icon 1902 of the switch OFF is displayed infrequently as in the first embodiment. The user pays attention to the display of the switch OFF icon 1902 from a series of displayed screens 1903. When the switch OFF icon 1902 is displayed, the user touches the switch OFF icon 1902 on the screen to turn off the alarm sound (FIG. 19D). When the alarm sound is turned off, the timer 119 notifies the cognitive function examination control section 109 of the fact, and the cognitive function examination control section 109 ends the cognitive function examination. The method for analyzing signs of dementia using the measured results is the same as in the first embodiment.

In addition to the above alarm operations, the cognitive function can be examined.

Every time the user turns pages with the use of an electronic book application installed on the smartphone of the present invention, a character or a pop-up determined in advance is displayed on a page or a specific page that the user is likely to be interested in (pages of a table of contents, section, chapter, illustrations, or pictures), or the page is changed with a different color. Then, all or part of the electroencephalogram during reading from when the book is opened to when the book is closed is measured, and P300 of the electroencephalogram when the page changes is analyzed. In that case, there is a need to set the frequency of pages that may be of interest to a certain value or less.

In that case, the image used as a target is a page screen that displays the predetermined character or pop-up together, and the image used as a standard is a page screen that does not display the character or pop-up.

In addition, the cognitive function examination is performed from a time when the electronic book application is executed on the smartphone and any two of the electroencephalogram measurement electrodes 302, 303, 306, and 307 are touched by the hand to an end of the electronic book application.

In addition, when viewing an image content on the smartphone of the present embodiment, the image (for example, a title of the content, or the like) related to the content to be viewed is mixed infrequently between the standard images in the oddball task storage section, which is not related to the viewing content at the start of reproduction, and reproduced.

Similarly, when changing the content being viewed, the same image reproduction method is performed immediately after the content change. As described above, the electroencephalogram during viewing when the image reproduction application in the smartphone is set as described above is measured, and P300 of the electroencephalogram when reproducing the image related to the content to be viewed is analyzed to examine the cognitive function.

In that case, the image used as the target, for example, a title of the content that the user is attempting to view, and the image used as the standard is data in the standard management table stored in the oddball task data storage section. As the standard, an image stored in another smartphone in advance may be used.

In addition, the cognitive function examination is performed from a time when any two of the electroencephalogram measurement electrodes 302, 303, 306, and 307 are touched with the hand when the content reproduction application is activated until the content reproduction or content change is completed.

In addition, favorite image and voice are registered as wallpaper or a start-up voice at the time of start-up, and the registered image and voice are reproduced after the image and voice not related to the startup end. The electroencephalogram at the time of start-up when the startup processing method in the smartphone is set as described above is measured, and P300 of the electroencephalogram when the favorite wallpaper and startup voice are reproduced is analyzed to analyze the cognitive function.

In that case, the image and voice to be used as a target are an image and voice which have already been set an image as the wallpaper, and the image and voice to be used as a standard are data in the standard management table stored in the oddball task data storage section. As the standard, the image and voice that are not registered as favorites and are stored in advance on the smartphone may be used.

In addition, the cognitive function examination is performed until the favorite wallpaper or start-up voice is displayed or reproduced at the end of start-up after touching any two of the electroencephalogram measurement electrodes 302, 303, 306, 307 with the hand at the time of start-up of the smartphone.

Also, when measuring with a thermometer or the like, an unrelated screen or voice is displayed or reproduced shortly before the measurement result is displayed, and then a screen for displaying the result is displayed, or a voice for reading the result is reproduced. The electroencephalogram during body temperature measurement when a body temperature measurement application in the smartphone is set as described above is measured, and P300 of the electroencephalogram when the measurement result is displayed or the measurement result is read out is analyzed and examined. The temperature sensor may be used by being connected to a smartphone or may be mounted inside.

In that case, the image or voice used as the target is a measurement result (image or voice) of the body temperature, and the image or voice used as the standard is data (image or voice) in the standard management table stored in the oddball task data storage section 103. The standard may use images or voices stored in advance in the smartphone.

The cognitive function examination is performed from the time when any two of the electroencephalogram measurement electrodes 302, 303, 306, and 307 are touched with the hand at the start of the body temperature measurement until the body temperature measurement result is displayed or reproduced.

Also, as a game, images such as characters are mixed at random at a low frequently between images such as symbols and displayed, and when the characters appear, the screen is touched or a button provided on the device is pressed. The electroencephalogram at the time of playing this game by the smartphone is measured, and P300 of the electroencephalogram when the characters are displayed on the screen is analyzed to examine the cognitive function.

As a game, a heterogeneous voice (instrumental voice, human voice, bird cry, vehicle horn, and so on) is mixed at random at a low frequency between single voices and reproduced. When the heterogeneous voice is reproduced, a button is pressed, and limbs are moved. The electroencephalogram when playing the game on the smartphone is measured, and the cognitive function is examined by analyzing the P300 of the electroencephalogram when the heterogeneous voice has been reproduced.

In that case, images such as the characters are used as a target, and an image in the standard management table stored in the oddball task data storage section is used as a standard. The standard may be an image stored in advance on the smartphone.

In addition, the cognitive function examination is performed from a time when any two of the electroencephalogram measurement electrodes 302, 303, 306, and 307 are touched with the hand at the start of the game until the game ends.

Although the application on the smartphone to which the present invention can be applied has been mainly described above, the claimed scope of the present invention is not limited to the above description. For example, the same as the smartphone is applied to a fixed phone. In addition, the same as during the incoming phone call of the smartphone according to the present invention can be applied to a display function for conformation of a visitor such as a door intercom.

Fourth Embodiment

In the embodiments described above, a smartphone-based shape is used as the cognitive function examination device. In the present embodiment, other shapes and forms will be described below.

First, a functional block diagram of a cognitive function examination system according to the present invention in which the electroencephalogram measurement section 105 of FIG. 1 is mounted on a measurement device will be described.

Figure 27:
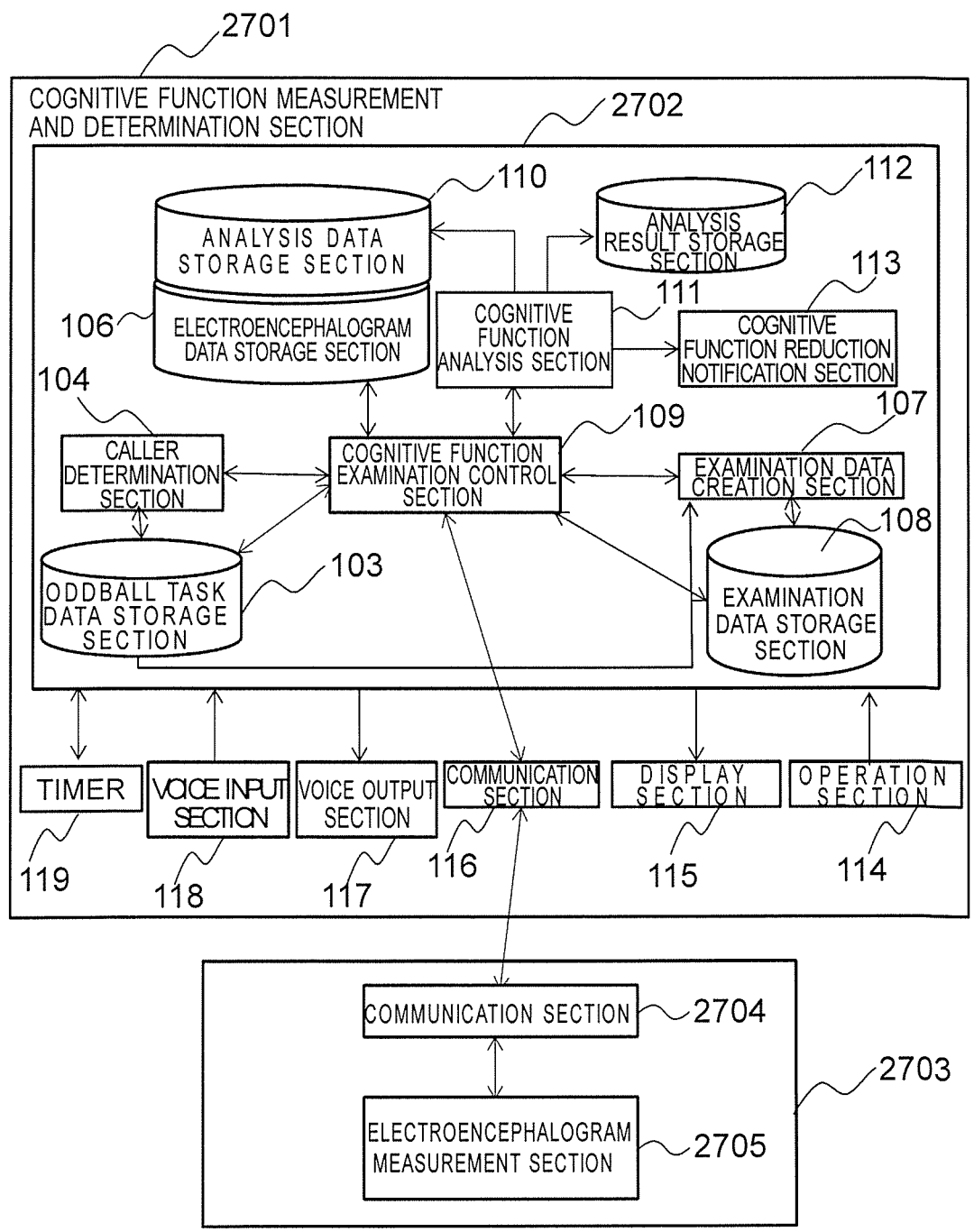
FIG. 27 is a functional block diagram of a cognitive function examination system in which an electroencephalographic measurement function is implemented into a measurement device.

FIG. 27 is a functional block diagram of a cognitive function examination system including a cognitive function measurement device and an electroencephalogram measurement device.

FIG. 27 shows a functional block diagram of a system realizing the present invention and including a smartphone case (FIG. 20), a frame of glasses or sunglasses (FIG. 21A), headphones (FIG. 22A), a hearing aid (FIGS. 23A and 23B), a mouse (FIG. 24A), a TV remote controller (FIG. 25A), which have an electroencephalogram measurement function, and a smartphone (FIG. 21B), a tablet PC (2110), a desktop PC, a notebook PC, an e-book TV main body (2111), a radio main body (2214), which have a cognitive function examination function, and so on, for realizing the present invention. The mouse is an example of an information input device, and a device associated with the mouse is an information processing device that operates according to operation information input from the mouse, such as a PC.

A main difference from the functional block diagram (FIG. 1) according to the first embodiment resides in that the electroencephalogram measurement section 105 is provided in a measurement device 2703 including an external device. Further, the measurement device 2703 provided with an electroencephalogram measurement section 2705 is also provided with a communication section 2704, and a cognitive function examination device 2701 such as a smartphone and the measurement device 2703 provided with the electroencephalogram measurement section 2705 are cooperated with each other through the communication section 2704.

Hereinafter, an example in which a smartphone (FIG. 21B) is used as a cognitive function examination device will be described.

Note that a communication between the cognitive function examination device 2701 and the measurement device 2703 including the electroencephalogram measurement section 2705 may be wired or wireless.

The cognitive function examination system according to the present invention includes the cognitive function examination device 2701 and the measurement device 2703.

The cognitive function examination device 2701 includes a cognitive function measurement and determination section 2702, an operation section 114, a display section 115, a communication section 116, a voice output section 117, a voice input section 118, and a timer 119.

The operation section 114 is used by the user to input an operation to the cognitive function examination device 2701.

The display section 115 displays an operation screen and various information for the user.

The communication section 116 communicates with external devices through various networks (telephone network, WiFi, Bluetooth, and so on). In the present embodiment, the communication section 116 functions as an electroencephalogram data acquisition section.

The voice output section 117 and the voice input section 118 perform voice output and input through a microphone or a speaker.

The timer 119 measures time such as a clock, an alarm, and a stopwatch.

The cognitive function measurement and determination section 2702 includes an oddball task data storage section 103, a caller determination section 104, an electroencephalogram data storage section 106, an examination data creation section 107, an examination data storage section 108, a cognitive function examination control section 109, and an analysis data storage section 110, a cognitive function analysis section 111, an analysis result storage section 112, and a cognitive function reduction notification section 113.

The oddball task data storage section 103 is a portion for storing data for the oddball task.

The oddball task data storage section 103 stores, for example, information about a person (watcher) who watches the user to be subjected to the cognitive function examination, for example, information on watcher's phone number, name, e-mail address, voice, and pictures.

When the caller determination section 104 receives a call or mail through the communication section 116, the caller determination section 104 determines whether or not the other party is a watcher registered in the oddball task data storage section 103.

The electroencephalogram data storage section 106 records the electroencephalogram measured by the measurement device 2703.

The examination data creation section 107 automatically generates data for cognitive function examination with the use of the watcher's voice and pictures stored in the oddball task data storage section 103, images such as pictograms and ringtones recorded in the smartphone in advance, and so on.

The examination data storage section 108 stores the examination data created by the examination data creation section 107.

The cognitive function examination control section 109 detects that a potential is detected from the electrodes in the measurement device 2703 and the electroencephalogram can be measured, starts the examination with the use of the examination data stored in the examination data storage section 108, and records the measured electroencephalogram in the electroencephalogram data storage section 106. In addition, the cognitive function examination control section 109 controls all parts configuring the cognitive function measurement and determination section 2702.

The analysis data storage section 110 stores data for analyzing and evaluating the cognitive function.

The cognitive function analysis section 111 analyzes the electroencephalogram measurement result recorded in the electroencephalogram data storage section 106, and compares the analyzed result with the data of the analysis data storage section 110 which is calculated in advance, to thereby perform the cognitive analysis.

The analysis result storage section 112 records the analysis result of the cognitive function analysis section 111.

When a reduction in the cognitive function is detected, and a sign of dementia is detected in the cognitive function analysis section 111, the cognitive function reduction notification section 113 notifies the watcher registered in advance in the oddball task data storage section 103 of the detection of the sign.

In this example, the watcher registered in the oddball task data storage section 103 is a person who casually watches the life and health of the user (elderly person) subjected to the cognitive function examination, for example, the user's family or care manager. With the use of the cognitive function examination device 2701 (smartphone), the watcher can watch the state of the cognitive function in the daily life of the user (elderly person) even from a remote place.

The data to be registered in the oddball task data storage section 103 may be existing address book data (phone number, name, address, e-mail address, etc.) of the smartphone, pictures recorded in an internal memory or an SD card, data (phone number, name, e-mail address, voice, pictures) recording in a call record, or data newly sent from the watcher and registered.

The measurement device 2703 includes the communication section 2704 and the electroencephalogram measurement section 2705.

The communication section 2704 communicates with external devices through various networks (WiFi, Bluetooth, and so on).

The electroencephalogram measurement section 2705 measures the electroencephalogram of the user to be subjected to the cognitive function examination.

As described above, in the cognitive function examination system according to the present embodiment, the cognitive function examination device 2701 includes, for example, a smartphone (FIG. 21B), a tablet PC 2110, a desktop PC, a notebook PC, an electronic book, a TV main body 2111, a radio main body 2214, and the like. The measurement device 2703 includes a smartphone case (FIG. 20A, FIG. 20B, FIG. 20C), a glasses or sunglasses frame (FIG. 21A), headphones (FIG. 22A), a hearing aid (FIGS. 23A and 23B), a mouse (FIG. 24A), a TV remote controller (hereinafter referred to as TV remote controller: FIG. 25A), and so on.

In the cognitive function examination system according to the present embodiment, hardware configuring the cognitive function examination and determination section 102 described in FIG. 2, for example, an electroencephalogram measurement electrode 221, a signal processing device 222, an ADC 223, a CPU 211, a ROM 212, a RAM 213, and a storage device 214 are mounted on either the cognitive function examination device 2701 or the measurement device 2703. The communication module 227 is mounted on both those devices.

However, the cognitive function examination device 2701 and the measurement device 2703 configuring the cognitive function examination system according to the present embodiment are not limited to the devices described above. Further, a communication between the cognitive function examination device and the electroencephalogram measurement device may be wireless or wired.

Hereinafter, functional blocks and hardware configurations will be described for each implementation example.

(Example of Smartphone Case)

FIG. 20 shows an example in which the electroencephalogram measurement section 2705 is mounted on a smartphone case. Portions other than the electroencephalogram measurement section 2705 in FIG. 1 are provided in the smartphone.

Figure 20A:
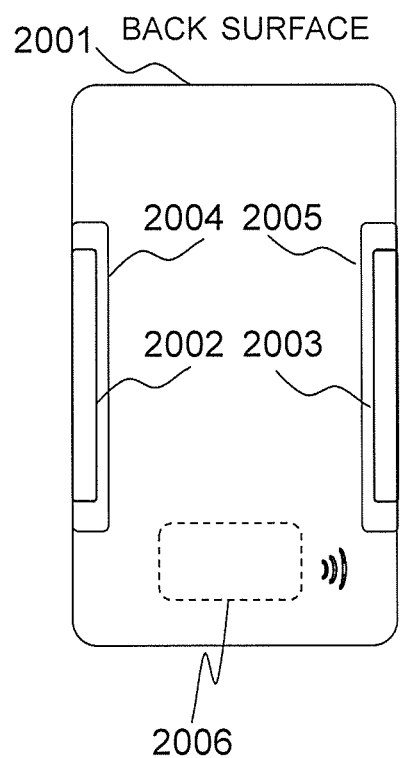
FIG. 20A is a rear view showing a mounting example of a cognitive function examination device smartphone case.
Figure 20B:
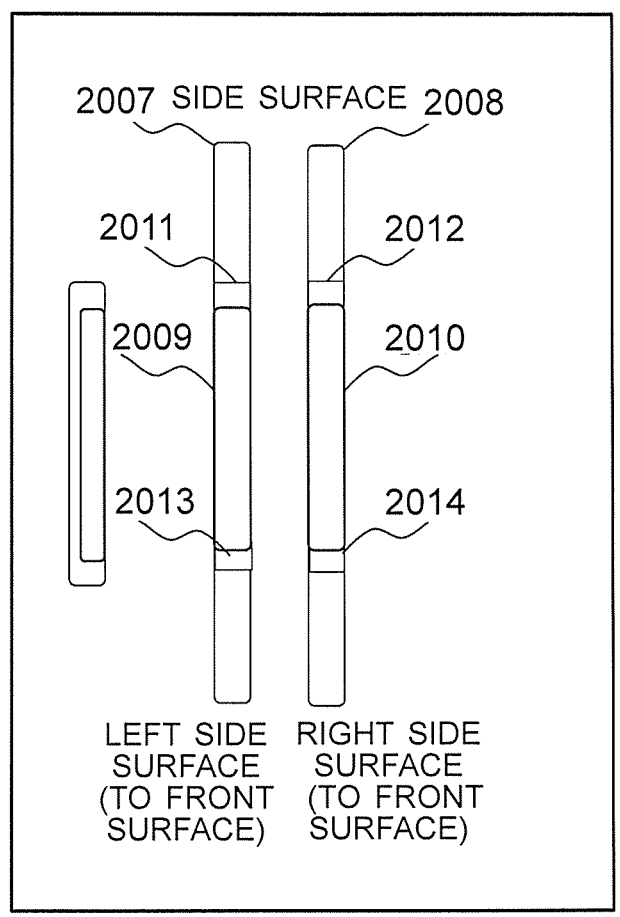
FIG. 20B is a side view showing a mounting example of the cognitive function examination device smartphone case.
Figure 20C:
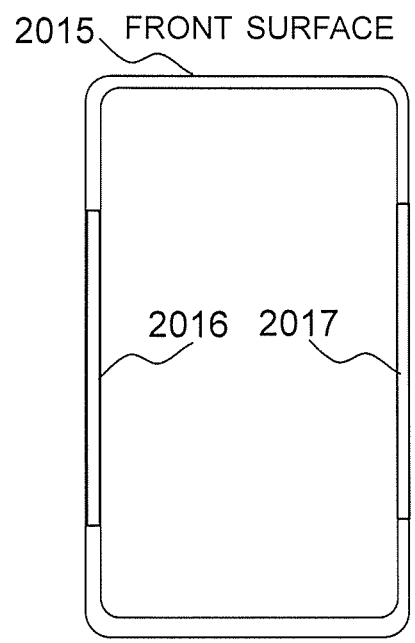
FIG. 20C is a front view showing a mounting example of the cognitive function examination device smartphone case.

FIGS. 20A, 20B, and 20C show a back surface, a side surface, and a front surface of the smartphone case, respectively.

The smartphone case (back surface 2001, left-side surface 2007, right-side surface 2008, front surface 2015) includes electroencephalogram measurement electrodes (electrodes 2002 and 2003 installed on the back surface, electrodes 2009 and 2010 installed on the side surface) and a signal processing device 222, an ADC 223, and a communication module 227 for transmitting the detected potential. The communication module 227 is a wireless communication module.

The signal processing device 222, the ADC 223, and the communication module 227 that transmits the detected potential are mounted on the back surface (reference numeral 2006). However, the mounting location is not limited to the position of 2006.

The electroencephalogram measurement electrodes are mounted with electrodes 2002 and 2003 at two locations on the back surface 2001 of the smartphone case. In addition, electrodes 2009 and 2010 are mounted at two locations on the left-side surface 2007 and the right-side surface 2008.

The electroencephalogram measurement electrodes at the above four locations, that is, the electrodes 2002 and 2003 disposed to the back surface, and the electrodes 2009 and 2010 disposed on the left and right sides can be combined according to a detection status of the potential (two electrodes are required for measurement in with bipolar induction).

Furthermore, a light is provided on the rear surface 2001, the left-side surface 2007, the right-side surface 2008, and the front surface 2015 of the smartphone case so as to border the electrodes. The figure shows lights 2004 and 2005 installed on the back surface, lights 2011, 2012, 2013 and 2014 installed on the side surfaces, and lights 2016 and 2017 installed on the front surface. Lights can have color variations. Light is illuminated with incoming, and clarifies the positions of the electroencephalogram measurement electrodes (the electrodes 2002 and 2003 disposed to the back surface, the electrodes 2010 and 2009 disposed on the right-side surface 2008 and the left-side surface 2007). In addition, since the location of the electroencephalogram measurement electrode can be shown in an easy-to-understand manner even in the dark due to lighting, the user can assume portions where the electroencephalogram measurement electrodes are disposed, that is, the electrodes 2002 and 2003 located on the side surfaces or the electrodes 2009 and 2010 located on the back surface. Also, since the lights 2004 and 2005 installed on the back surface, the lights 2011, 2012, 2013, and 2014 installed on the side surfaces, and the lights 2016 and 2017 installed on the front surface are mounted on the back surface 2001, the left-side surface 2007, the right-side surface 2008, and the front surface 2015 of the smartphone, accurately notify the user can be notified accurately of the incoming call and the location of the electrodes regardless of the state of the smartphone.

Figure 20D:
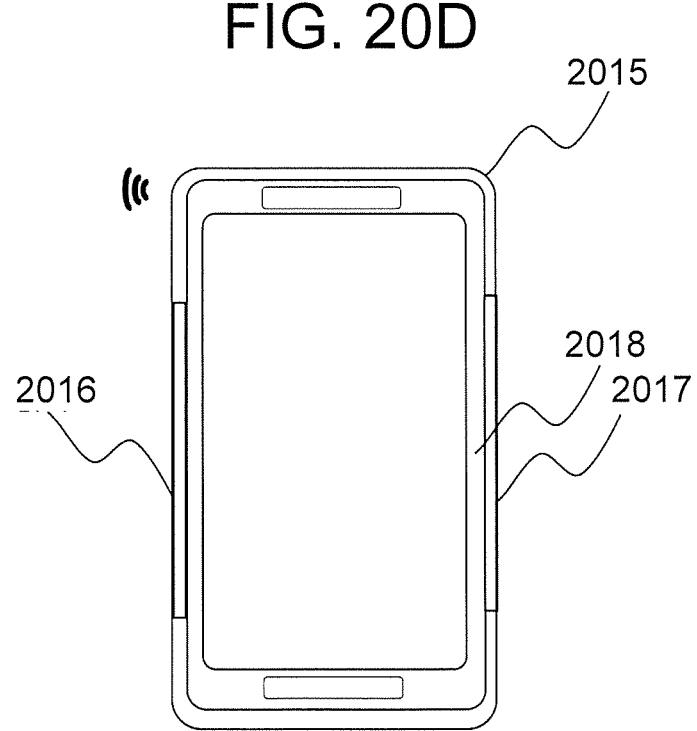
FIG. 20D is a front view showing a mounting example (at the time of smartphone mounting) of the cognitive function examination device smartphone case.

FIG. 20D is a view of the smartphone case (back surface 2001, right-side surface 2008, left-side surface 2007, front surface 2015) mounted on the smartphone 2018 and viewed from the front surface.

In the cognitive function examination system with the smartphone 2018 and the smartphone case (back surface 2001, right-side surface 2008, left-side surface 2007, front surface 2015), the alarm, the e-book page turning, the image content reproduction, the smartphone start-up process, the temperature measurement, and the game shown in the third embodiment can be implemented.

(Example of Glasses Frame)

Figure 21A:
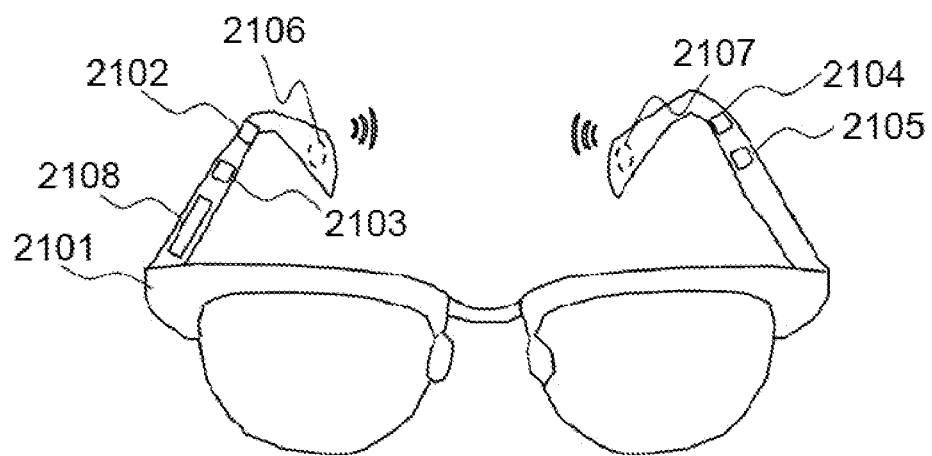
FIG. 21A is a diagram showing a mounting example in eyeglasses or sunglasses frame equipped with an electroencephalogram measurement function.
Figure 21B:
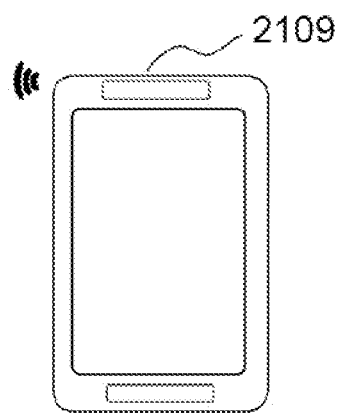
FIG. 21B is a front view of a cognitive function examination device (smartphone) that cooperates with the eyeglasses or sunglasses frame.

FIG. 21A shows an example in which the electroencephalogram measurement section 105 in the cognitive function examination device 101 according to the present invention is mounted on a frame 2101 of glasses or sunglasses.

In the following description, glasses will be described as an example. The glasses equipped with the electroencephalogram measurement section 2705 includes electrodes (2102, 2103, 2104, 2105) and a signal processing device 222 for measuring the electroencephalogram, an ADC 223, and a communication module 227 that transmits a detected potential wirelessly, in the frame 2101.

In this example, the four electrodes on the glasses frame can be used in combination as bipolar electrodes depending on a contact state with the body at the time of wearing. The electroencephalogram can be measured when at least two places are in contact with the body. The four electrodes (2102, 2103, 2104, 2105) can measure the electroencephalogram of up to 3 channels (for example, 1 channel with 2102 and 2103, 1 channel with 2104 and 2105, 1 channel with 2102 and 2104 or 2105 in combination). In order to measure the electroencephalogram of three channels, there is a need to bring all the electrodes in contact with the body.

Since AD has been known to deteriorate from a temporal lobe, measurement is performed with priority given to the combination of the electrodes 2102 and 2103 or the combination of electrodes 2104 and 2105. Alternatively, priority is given to measurement results obtained by combinations thereof. The signal processing device 222, the ADC 223, and the communication module 227 that wirelessly transmits the detected potential are provided at end portions of the frame (2106, 2107). The implementation locations of the signal processing device 222, the ADC 223, and the communication module 227 are not limited to the end portions 2106 and 2107.

The measured electroencephalogram potential is signal-processed and amplified, converted into a digital signal, transferred to the smartphone 2109 previously paired, and processed. If potentials are not detected by all the electrodes depending on how the glasses are worn, a warning is issued on the screen of the smartphone 2109 to notify the user of this fact. A small battery 2108 provided in the frame 2101 is used for supplying electricity.

As the cognitive function examination device that cooperates with the frame 2101, in addition to the smartphone, for example, an e-book, a tablet PC 2110, TV, and a PC are applied.

Figure 21C:
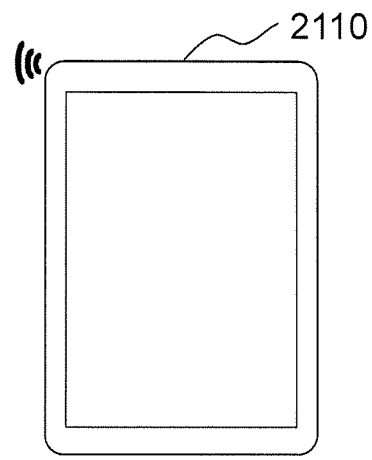
FIG. 21C is a front view of a cognitive function examination device (tablet PC) that cooperates with the eyeglasses or sunglasses frame.
Figure 21D:
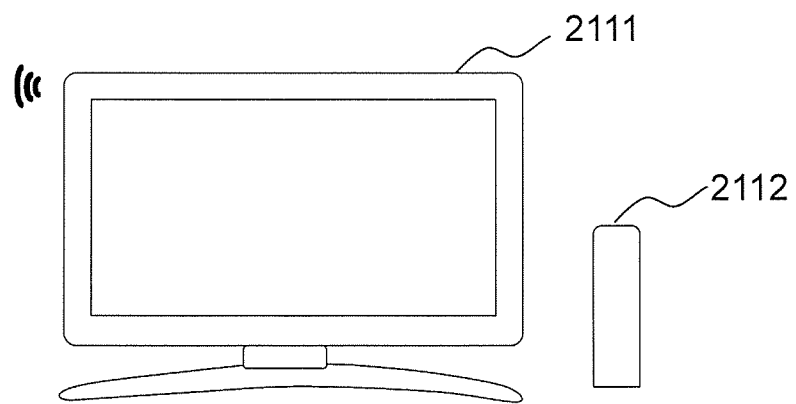
FIG. 21D is a front view of a cognitive function examination device (TV set) that cooperates with the eyeglasses or sunglasses frame.

FIG. 21C shows an example of the tablet PC 2110 that cooperates with the frame 2101, and FIG. 21D shows an example of the TV set (TV main body 2111 and remote controller 2112) that cooperates with the frame 2101. The TV set includes the TV main body 2111 and the remote controller 2112.

In the cognitive function examination system including the frame 2101 and the smartphone 2109, the e-book, the tablet PC 2110, the TV set (TV main body 2111, remote control 2112), the PC (desktop PC, notebook PC, etc., not shown), the alarm, electronic book page turning, image content reproduction, start-up processing, temperature measurement, and game shown in the embodiment can be implemented.

(Example of Headphones)

FIG. 22 shows an example in which the electroencephalogram measurement section 105 in the cognitive function examination device 101 according to the present invention is mounted on the headphones. A headband 2201 of the headphones is provided with electroencephalogram measurement electrodes (2202, 2203, 2204, 2205, 2206). Ear pads (2207, 2208) are also provided with electrodes 2209. A cloth type electrode is used for the electrodes of the ear pads (2207, 2208). With the placement of a large number of electrodes, the electroencephalogram can be measured over a wide range of the head. A signal processing device, a potential amplifier, an analog-digital converter, and a wireless module are provided in both housings (2210, 2211) (for example, mounted on a portion 2212. Similarly mounted on a housing 2211).

The detected potential is processed by the signal processing devices 222, ADCs 223 provided in the housings (2210, 2211), and transmitted to the smartphone 2109 from the communication modules provided in the housings (2210, 2211).

In order to simultaneously measure the electroencephalogram of multiple channels, a buffer memory may be provided on the headphone side, and the measured electroencephalogram may be buffered and then transmitted to the smartphone 2109.

Figure 22A:
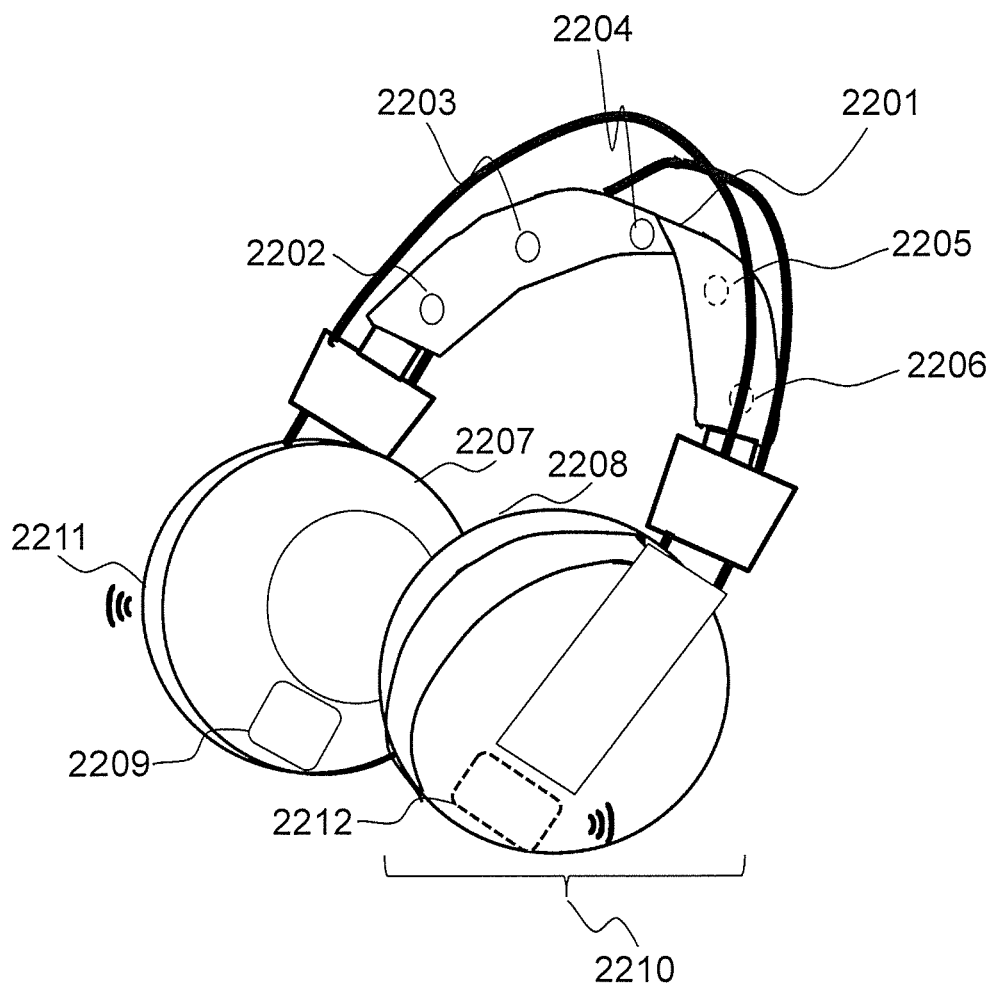
FIG. 22A is a diagram showing headphones equipped with an electroencephalogram measurement function.
Figure 22B:
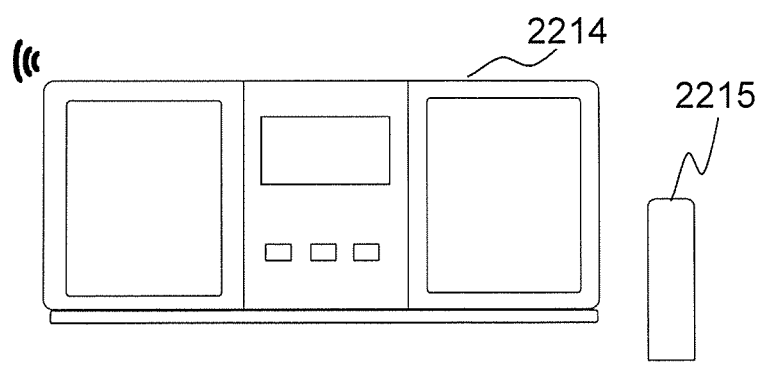
FIG. 22B is a diagram showing a cognitive function examination device (radio set) that cooperates with headphones equipped with an electroencephalogram measurement function.

In the headphone of FIG. 22A, the electrode used at the time of measurement can be selected according to the method of detecting the potential of the electroencephalogram.

Both unipolar and bipolar induction can be performed.

In the unipolar induction, the electrodes 2209 and 2212 coming in contact with earlobes are set as reference potentials, and can be combined with the five electrodes attached to the head band. In that case, the electroencephalograms of up to 5 channels can be measured (combination of 2209 and any of 2202, 2203, 2204, 2205, and 2206).

In the bipolar induction, the electroencephalogram of up to 4 channels can be measured (1 channel by combination of 2202 and 2203, 1 channel by combination of 2203 and 2204, 1 channel by combination of 2204 and 2205, and 1 channel by combination of 2205 and 2206).

In the headphone, the electroencephalogram measurement can be performed for the multiple channels with the combination of the two electrodes as described above. The electroencephalogram is measured using two electrodes with excellent potential detection.

As described above, the headphone can measure the electroencephalogram of up to five channels from a combination of the multiple electrodes whose potentials are detected.

Since AD has been known to deteriorate from the parietal lobe, priority is given to measurement of the electroencephalogram from 2203, 2204, and 2205 electrodes. In other words, the measurement of the combination of 2203 and 2204 and the combination of 2204 and 2205, or the measurement of the combination of the electrodes 2209 and any of 2203, 2204, and 2005 is given priority. In addition, the measurement results at that time are given priority for use in examinations.

Similarly, the electrode 2209 of the pad 2207 portion may be provided in 2208 as well.

In this case, whether the electrode 2209 is used as the reference electrode or the electrode on the 2208 side is used as the reference electrode can be selected according to the mounting state. In addition to the smartphone, the cognitive function examination device linked with the headphones (FIG. 22A) includes, for example, the radio (radio main body 2214, remote controller 2215), the tablet PC 2110, the TV set (TV main body 2111, remote controller 2112), and the PC shown in FIG. 22B.

Even in the cognitive function examination system using the headphones, the alarm, the electronic book page turning, the image content reproduction, the startup processing, the temperature measurement, and the game shown in the third embodiment can be implemented.

(Example of Hearing Aid)

FIG. 23 shows an example in which the electroencephalogram measurement device 2703 according to the present invention is mounted on a hearing aid.

In addition to the smartphones, devices capable of cooperating with the hearing aid of FIG. 23 include a radio set (radio main body 2214, remote controller 2215), a TV set (TV main body 2111, remote control 2112), a tablet PC 2110, a PC, and the like.

Figure 23A:
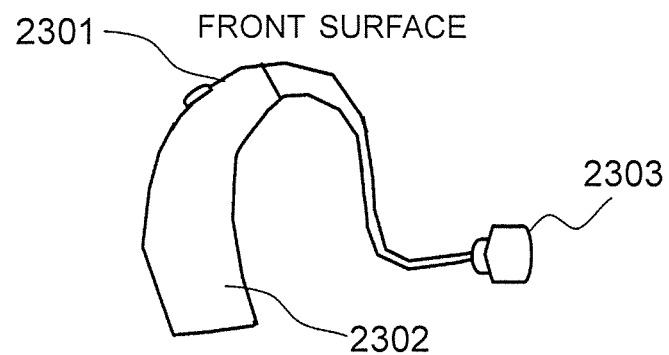
FIG. 23A is a front surface view showing a hearing aid equipped with an electroencephalographic measurement function.
Figure 23B:
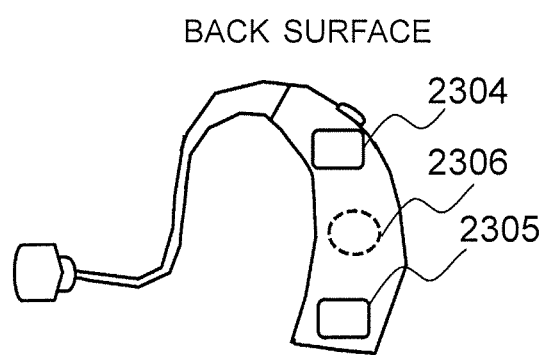
FIG. 23B is a rear surface view showing the hearing aid equipped with the electroencephalographic measurement function.

FIG. 23A shows a surface of an ear-mounted hearing aid 2301 on which the electroencephalogram measurement section 2705 is mounted. FIG. 23B is a rear view of the ear-mounted hearing aid 2301. FIG. 23A is a diagram when the ear-mounted hearing aid 2301 is worn. The ear-mounted hearing aid 2301 is used by putting a device on the ear ring portion.

The ear-mounted hearing aid 2301 includes a hearing aid main body 2302 and an ear mold 2303.

Electroencephalogram measurement electrodes (2304, 2305) are provided on the back surface of the ear-mounted hearing aid main body (in contact with the head). The hearing aid main body 2302 includes a signal processing device 222 that processes and amplifies the detected potential, an ADC 223, and a communication module 227 (those components are mounted on the hearing aid main body 2302. For example, those components are mounted on the portion 2306).

One-channel electroencephalogram can be measured by bipolar induction using two electrodes (2304, 2305).

The hearing aid is to in some cases to be used in pairs, or to be used on only one side. When used as a pair, the electrode to be used at the time of measurement may be selected depending on the state of potential detection. When paired, the electroencephalogram of up to 2 channels can be measured at maximum.

Figure 23C:
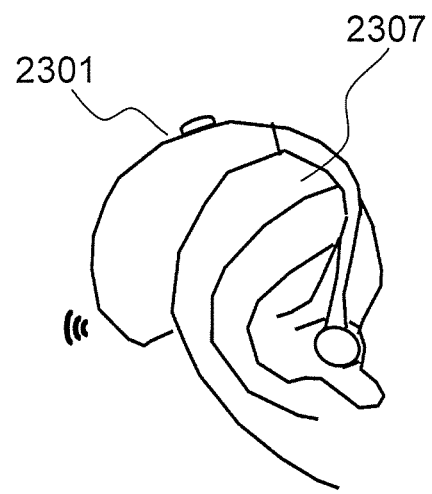
FIG. 23C is a diagram showing a wearing state of the hearing aid equipped with the electroencephalographic measurement function.

FIG. 23C shows an example of wearing the ear-mounted hearing aid. The ear-mounted hearing aid 2301 may be used on one side or in a pair, but even when only one side is used, the electroencephalogram is measured and the measurement result is transmitted to a paired smartphone in advance. Also, in the cognitive function examination system in which the ear-mounted hearing aid 2301 is cooperated with a smartphone or the like, the alarm, the image content reproduction, the startup processing, the temperature measurement, and the game shown in the third embodiment can be implemented.

(Example of Mouse)

Figure 24A:
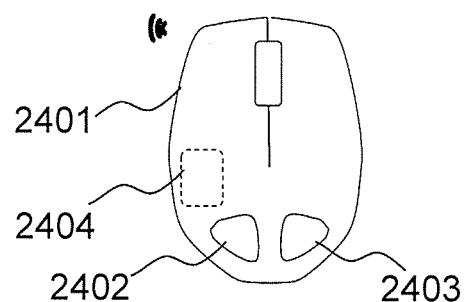
FIG. 24A is a front surface view showing a mouse equipped with the electroencephalographic measurement function.
Figure 24B:
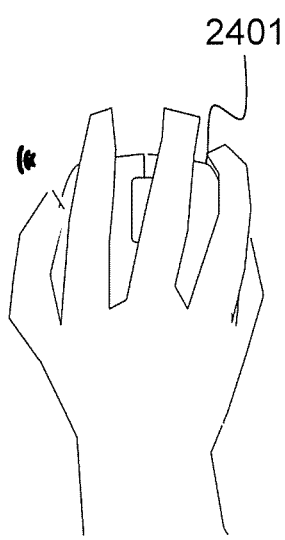
FIG. 24B is a diagram showing a use state of the mouse equipped with the electroencephalographic measurement function.
Figure 25A:
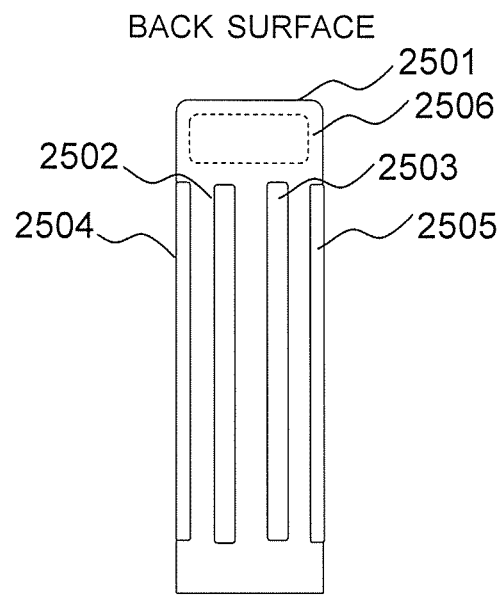
FIG. 25A is a rear view of a television remote controller equipped with the electroencephalographic measurement function.

FIGS. 24A and 24B show an example in which the electroencephalogram measurement section 2705 in the electroencephalogram measurement device 2703 according to the present invention is mounted on the wireless mouse 2401. The mouse may be wireless or wired. Hereinafter, the wireless mouse 2401 will be described as an example.

As shown in FIGS. 24A and 24B, the electroencephalogram measurement electrodes (2402, 2403) are disposed on the surface of the wireless mouse 2401 so as to be firmly in contact with two places on the inner skin of the hand during PC operation.

(Example in which Electroencephalogram Measurement Section 105 is Mounted on TV Remote Controller 2501)

Figure 25B:
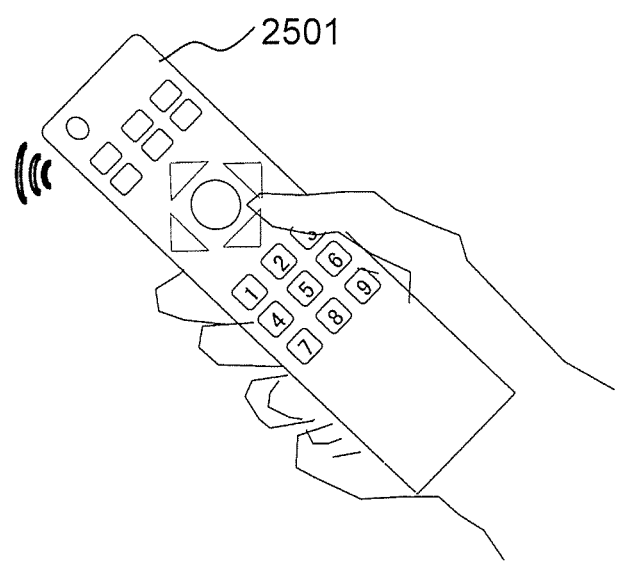
FIG. 25B is a diagram showing a use state of the television remote controller equipped with the electroencephalographic measurement function.

In the TV remote controller (FIGS. 25A and 25B) 2501 in which the electroencephalogram measurement section 2705 is mounted, the electroencephalogram measurement electrodes (2502, 2503, 2504, 2505) are disposed at locations where the hand is likely to come in contact with the electroencephalogram measurement electrodes at the time of using the TV remote controller. The electroencephalogram is measured (measured by bipolar induction) by detecting the potential from the two electrodes (any combination of 2502, 2503, 2504, and 2505) which are in contact with the hand during remote control operation.

The TV remote controller 2501 cooperates with the TV main body operated by the remote controller. Specifically, the measured potential of the electroencephalogram is signal-processed and amplified, converted into a digital signal, transferred to a TV main body that has been paired in advance, and processed.

If no potential is detected by the electroencephalogram measurement electrodes 2502, 2503, 2504, and 2505 depending on how the TV remote controller 2501 is held, a warning is given to the TV main body screen to notify the user of this fact.

In the cognitive function examination system including the TV remote controller 2501 and the TV main body, the alarm, the image content reproduction, and the game shown in the third embodiment can be implemented.

(Example of Small Robot)

FIG. 26 shows an example in which the cognitive function examination device 101 according to the present invention is mounted on a small interactive robot 2601.

Figure 26A:
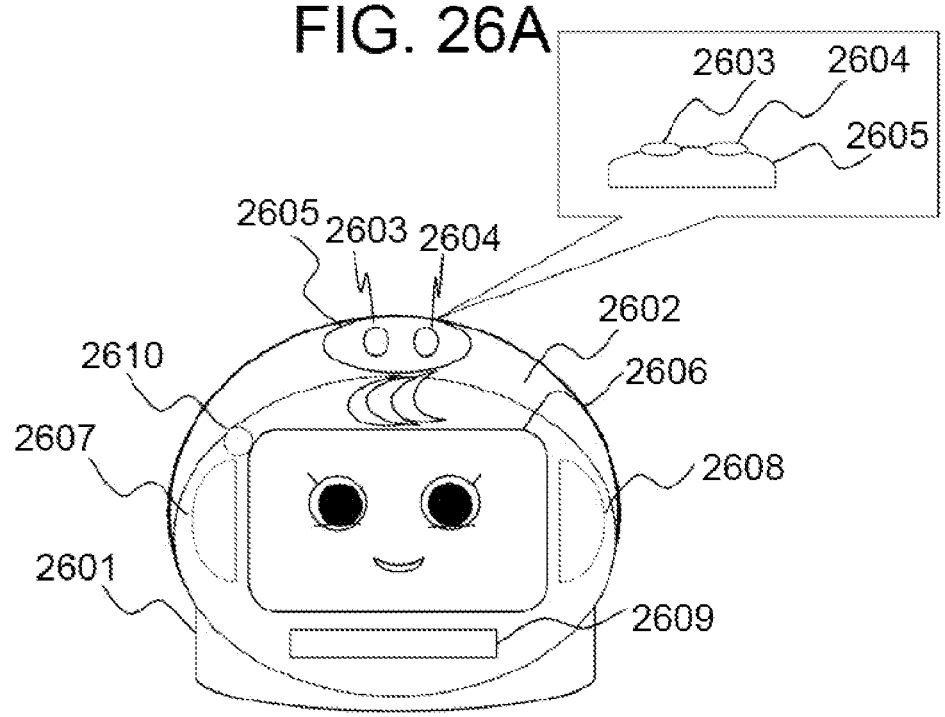
FIG. 26A is a front view showing a mounting example of a cognitive function examination device (robot).
Figure 26B:
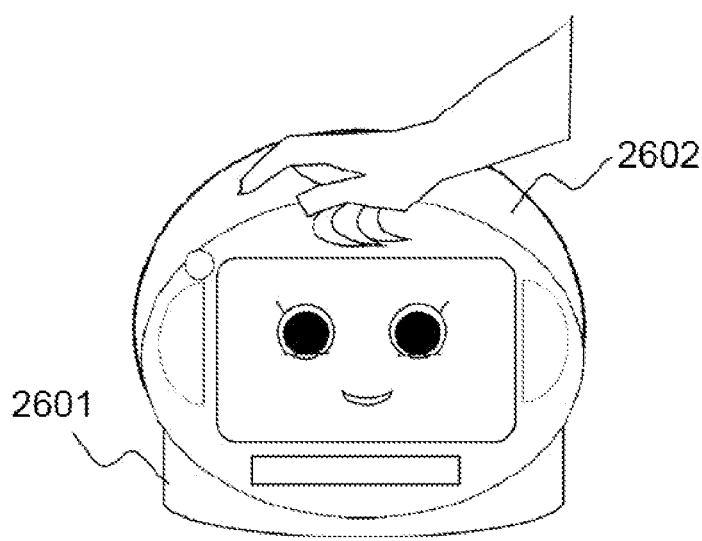
FIG. 26B is a diagram showing a use state of the mounting example of the cognitive function examination device (robot).

FIG. 26A shows a configuration of the robot 2601, and FIG. 26B shows an example of measuring an electroencephalogram with the use of the robot 2601. A head 2602 of the robot 2601 is provided with electroencephalogram measurement electrodes 2603 and 2604. The robot 2601 has a built-in control device made up of hardware such as a CPU, and the control device functions as a cognitive function examination device.

A portion (reference numeral 2605) in which the electroencephalogram measurement electrodes are mounted is three-dimensional and easy to handle. The electroencephalogram measurement electrodes 2603 and 2604 are mounted on the surface of the three-dimensional portion (reference numeral 2605). The electroencephalogram potential is measured with bipolar induction. The installed electrodes are not limited to two electrodes. The electrodes are disposed so as to easily act as an interface (the hand is placed on the electrodes in a motion of stroking the child's head). The electrodes are disposed in a place where the user can enjoy the operation without feeling discomfort in daily life.

In front of the head 2602 of the robot 2601, a display 2606 for operation and display, voice reproduction speakers (2607, 2608), a microphone 2609 for collecting voice from the user, and a small camera 2610 for identifying the user are provided.

When the hand is placed on the three-dimensional part 2605 of the head 2602, the electroencephalogram potential is detected, and an oddball task is displayed on the display 2606 that displays the expression of the robot 2601. Alternatively, a voice for the oddball task is reproduced from the speakers (2607, 2608). The speakers (2607, 2608) are provided in two places on the left and right sides of the display 2606 for the operation and display in order to present a task for determining the directionality of the voice. In addition, the microphone 2609 is mounted below the display 2606. The location of the microphone or speaker is an example, and the present invention is not limited to the above configuration.

FIG. 26B shows an operation at the time of measuring an electroencephalogram. The hand is placed on the electroencephalogram measurement electrodes 2603 and 2604 of the head 2602 of the robot 2601, to thereby detect the potential of the electroencephalogram from the skin of the hand and start the measurement. The hand is kept to be placed on the electroencephalogram measurement electrodes 2603 and 2604 during the execution of the oddball task.

While the robot is talking to the user, the hand may be guided so as to be placed on the head electrodes when performing the oddball task when receiving an incoming call or playing a game.

In the small robot 2601, the alarm, the electronic book page turning, the image content reproduction, the startup processing, the temperature measurement, and the game shown in the third embodiment can be performed.

Fifth Embodiment

In a fifth embodiment, an example of services leveraging cognitive function examination device with the use of an electroencephalographic technique according to the above embodiments will be described.

(Application Example to Watch or Prevention Service and Medical Service)

Figure 28:
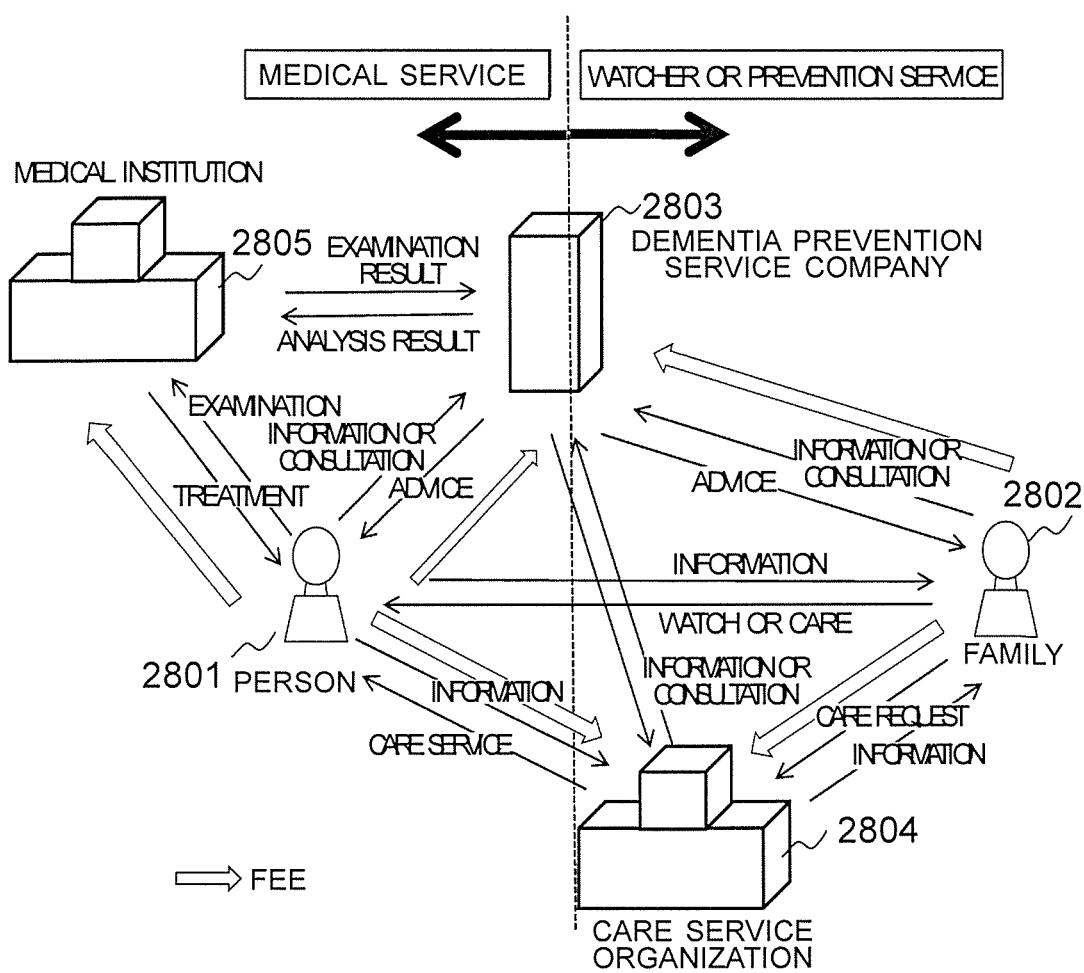
FIG. 28 is a diagram showing an example of a service leveraging the cognitive function examination device and a cognitive function examination system.

FIG. 28 shows an overview of the watch or prevention service and the medical service. The users of this service are a person who receives the service related to the monitoring, maintenance, and improvement of the state of cognitive function (hereinafter referred to as a person 2801) and his family 2802. There are two purposes of the service provided by the cognitive function examination device of the present invention.

The first purpose is to measure the cognitive function of a healthy person who has not developed dementia, thereby being capable of equipped with measures for founding a reduction in the cognitive function early and preventing the onset of dementia in advance. Medical practice that takes measures before the onset of the disease is called preemptive medicine and is included in medical practice. Today, in preemptive medicine, with the utilization of not only the data measured by the cognitive function examination device according to the present invention but also big data including genetic data and lifestyle habits, the discovery of new knowledge on the cause of disease and improvement items is expected.

Another purpose is to regularly measure the cognitive function to observe the course of symptoms, the measurement of treatment, and the course of treatment when cognitive function reduction is observed or when dementia is affected.

The watch or prevention service is provided to achieve the former purpose. The watch or prevention service includes a dementia prevention service company 2803, the person 2801 who receives the service, and his family 2802. In some situations, a care service organization 2804 is added to this configuration.

The person 2801 and his family 2802 (both, or only the person or only the family) join the dementia prevention service company 2803 that monitors the state of cognitive function and checks whether or not there is any abnormality in the cognitive function based on the measurement result of cognitive function. Furthermore, the person 2801 and his family 2802 join the care service organization 2804 as necessary. A service fee with respect to the dementia prevention service company may be paid by the person 2801 or family 2802. The family 2802 is positioned to watch over the person 2801. Whether the person 2801 is being watched may or may not be known.

The dementia prevention service company 2803 collects data measured from the cognitive function examination device of the present invention and analyzes the data to grasp the state of the cognitive function of the person 2801, and provides analysis results and advice to the person 2801 or his family 2802. The dementia prevention service company 2803 consults with the person 2801 or his family 2802 and gives answers.

When the person 2801 is a member of the care service organization 2804, the care service organization 2804 obtains the permission of the person 2801 or his family 2802 and sends data or information such as the daily life of the person 2801 to the dementia prevention service company 2803, and can receive advice on nursing care of the person 2801. In addition, if necessary, consultation on measures for preventing dementia and the like can be made, and an answer to the consultation can be obtained from the dementia prevention service company 2803.

The care service organization 2804 provides a care service to the person 2801 based on advice obtained from the dementia prevention service company 2803. For example, if daily exercise and recreation help an improvement in the cognitive function, such care services are implemented. Further, in order to confirm the effect on the cognitive function following the implemented services, the results of the measurement of the cognitive function in cognitive function examination device according to the present invention are provided to the dementia prevention service company 2803, and the information on the results is also provided to his family. If the person does not have a family, or if the person wishes, the information may be provided directly to the person 2801.

The care service organization 2804 can also receive a specific request for the contents of the care service from the family by providing the family 2802 with daily information on the person 2801.

The above description is given of an example in which the cognitive function examination device and the cognitive function examination system according to the present invention are applied to the watch service. (This example corresponds to a right-side of a dashed line of FIG. 28).

Next, a medical service is provided to achieve the latter purpose. The medical service is provided by a dementia prevention service company 2803, and a medical institution 2805 that conducts examinations and treatments for dementia and its early stage mild cognitive impairment and cognitively impaired healthy persons. In some situations, the care service organization 2804 is added to this configuration.

The dementia prevention service company 2803 and the medical institution 2805 share the information about the person with the consent of the person 2801 and his family 2802 and provide the services. The person 2801 and his family 2802 (both or only the person or only the family) join the dementia prevention service company 2803 that provides advice to the person 2801 and their family 2802 in cooperation with the medical institution 2805 when an abnormality is recognized in the cognitive function.

The medical institution 2805 performs a close examination and diagnoses when the cognitive function reduction is observed. In addition, measures for treatment and prevention will be implemented according to the diagnosis results.

The watch service described above is a service when the reduction of the cognitive function which is a main problem is not observed. The watch service detects a reduction in the cognitive function, and starts a cooperation with the medical institution 2805 only when an abnormality has been detected. The watch service is a screening orientation and is not intended to perform diagnostic. However, when a reduction in the cognitive function is detected and has not yet reached a stage of dementia, measures are actively taken in cooperation with the medical institution 2805.

The dementia prevention service company 2803 implements an appropriate service for members of the service (person 2801 and his family 2802) based on the enormous amount of data that has been acquired from the members. However, medical practices are implemented in cooperation with medical institution 2805.

The dementia prevention service company 2803 collects data about the effects on the medical practice and the provided service, generate hypotheses about a mechanism and the measures of developing dementia that has not yet been elucidated from analysis of the data, and can provide the hypotheses to the medical institutions 2805. Today, AI is taking on the role of big data analysis, and it is expected to discover new knowledge and generate hypotheses.

The medical institution 2805 determines diagnostic, measures and treatment based on the analysis results of enormous data and information by the AI.

The knowledge obtained from the analysis results of the data and information can be directly provided to the members (the person 2801 and his family 2802) as long as the knowledge falls outside the scope of medical practice. The medical institution 2805 provides the medical practice. A boundary between the medical practice and the non-medical practice varies depending on the scope of medical practice for dementia and is not clear. This is because the range of medical practice may change over time.

Another application example of the cognitive function examination device according to the present invention is a vehicle driving ability (based on the cognitive function) examination or periodic monitoring service mainly for elderly people. For example, there is a need to periodically confirm the reaction to the stimulus and the ability to determine the situation other than when updating the driver's license of the elderly person.

LIST OF REFERENCE SIGNS

101: cognitive function examination device
102: cognitive function measurement and determination section
103: oddball task data storage section
104: caller determination section
105: electroencephalogram measurement section
106: electroencephalogram data storage section
107: examination data creation section
108: examination data storage section
109: cognitive function examination control section
110: analysis data storage section
111: cognitive function analysis section
112: analysis result storage section
113: cognitive function reduction notification section

The invention claimed is:

1. An electroencephalogram data analysis system comprising:
an electronic device including a processor, the processor being configured to present, to a subject, examination data that is used for examining a cognitive function of the subject at a time the subject is executing an operation that has a purpose different from a purpose of measuring an electroencephalogram of the subject; and
a measurement device including i) an electroencephalogram detection sensor configured to acquire electroencephalogram data from the subject while the examination data is being presented to the subject, and ii) a wireless transmitter configured to transmit, to the electronic device, the electroencephalogram data acquired by the electroencephalogram detection sensor, wherein the processor is configured to:
receive the electroencephalogram data from the measurement device; and
detect an index of the cognitive function of the subject from the electroencephalogram data of the subject,
wherein the processor is further configured to:
extract predicates from one of contents of the subject's speech and outgoing mails sent by the subject in the past to classify the extracted predicates as a visual sense predicate or an auditory sense predicate by referring to a corpus,
calculate a frequency of use of the visual sense predicates or a frequency of use of the auditory sense predicates,
determine whether a predominant sense of the subject is a visual sense or an auditory sense based on the calculated frequency of use of the visual sense predicates or the calculated frequency of use of the auditory sense predicates, and
determine whether to use a visual image or an auditory voice as the examination data to examine the cognitive function of the subject based on the determined predominant sense of the subject.

2. The electroencephalogram data analysis system according to claim 1, wherein the measurement device is glasses or sunglasses provided with the electroencephalogram detection sensor and the wireless transmitter.

3. An electronic device that acquires and analyzes electroencephalogram data of a subject, comprising a processor configured to:
present to the subject examination data used for examining a cognitive function of the subject while the subject executes an operation that has a purpose different from a purpose of measuring an electroencephalogram of the subject;
receive electroencephalogram data of the subject, the electroencephalogram data being acquired from the subject while the examination data is being presented to the subject; and
detect an index of the cognitive function of the subject from the electroencephalogram data of the subject,
wherein the processor is configured to:
extract predicates from one of contents of the subject's speech and outgoing mails sent by the subject in the past to classify the extracted predicates as a visual sense predicate or an auditory sense predicate by referring to a corpus,
calculate a frequency of use of the visual sense predicates or a frequency of use of the auditory sense predicates,
determine whether a predominant sense of the subject is a visual sense or an auditory sense based on the calculated frequency of use of the visual sense predicates or the calculated frequency of use of the auditory sense predicates, and
determine whether to use a visual image or an auditory voice as the examination data to examine the cognitive function of the subject based on the determined predominant sense of the subject.

4. The electronic device according to claim 3, further comprising an analysis data storage section that stores cognitive function analysis data calculated in advance for comparison with the electroencephalogram data of the subject,
wherein the processor is configured to output a comparison result of the electroencephalogram data of the subject and the cognitive function analysis data.

5. The electronic device according to claim 4, wherein the processor is configured to notify a person concerned about the subject registered in advance of the comparison result when the comparison result satisfies a predetermined notification criterion.

* * * * *